United States Patent [19]

Karger et al.

[11] 4,036,863
[45] July 19, 1977

[54] TRINAPTHYLMETHANE COMPOUNDS

[75] Inventors: Eva R. Karger, Arlington; Paul T. MacGregor, Lexington, both of Mass.

[73] Assignee: Polaroid Corporation, Cambridge, Mass.

[21] Appl. No.: 691,889

[22] Filed: June 1, 1976

Related U.S. Application Data

[63] Continuation-in-part of Ser. No. 456,870, April 1, 1974, Pat. No. 3,976,662, which is a continuation-in-part of Ser. No. 202,615, Nov. 26, 1971, Pat. No. 3,816,453.

[51] Int. Cl.$^2$ .................. C07C 39/14; C07C 39/16
[52] U.S. Cl. ........................ 260/386; 260/326.13 R
[58] Field of Search ........................................ 260/386

[56] References Cited

U.S. PATENT DOCUMENTS 1,460,315  6/1923  Montmollin et al. ............... 260/386

FOREIGN PATENT DOCUMENTS 191,854   1/1923  United Kingdom ................ 260/386
289,564   5/1928  United Kingdom ................ 260/386
325,933   3/1930  United Kingdom ................ 260/386

*Primary Examiner*—Allen B. Curtis
*Attorney, Agent, or Firm*—Sybil A. Campbell

[57] ABSTRACT

This invention relates to derivatives of phthalaldehydic and naphthalaldehydic acid useful as intermediates in the preparation of pH-sensitive phthalide and naphthalide indicator dyes.

A class of intermediates provided by the present invention comprises compounds of the formula:

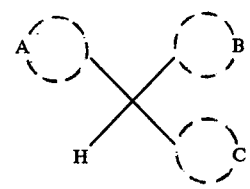

wherein A represents 4'-hydroxy-1'-naphthyl; B represents 4'-hydroxy-1'-naphthyl or indol-3-yl and C represents a 2-carboxy-1-phenyl radical or an 8-carboxy-1-naphthyl radical and preferably is 8-carboxy-1-naphthyl.

13 Claims, No Drawings

TRINAPTHYLMETHANE COMPOUNDS

CROSS-REFERENCE TO RELATED PATENT APPLICATIONS

This application is a continuation-in-part of our copending application Ser. No. 456,870, filed Apr. 1, 1974, now U.S. Pat. No. 3,976,662 which, in turn, is a continuation-in-part of our application Ser. No. 202,615 filed Nov. 26, 1971, now U.S. Pat. No. 3,816,453.

BACKGROUND OF THE INVENTION

1. Field of the Invention

This invention relates to a novel method of preparing indicator dyes and to novel intermediates useful in the preparation thereof.

2. Description of the Prior Art

Dyes which undergo a change in spectral absorption characteristics in response to a change in pH are well known in the art, and frequently, are referred to as indicator or pH-sensitive dyes. Typically, these dyes change from one color to another, from colored to colorless or from colorless to colored on the passage from acidity to alkalinity or the reverse and are commonly employed in analytical chemical procedures to measure changes in pH value. Among the indicator dyes most widely used is the group derived from phthaleins as exemplified by phenolphthalein, thymolphthalein, cresolphthalein and 1-naphtholphthalein.

Though various methods have been used for synthesizing phthalein indicator dyes, they are generally prepared via the Friedel-Crafts reaction by condensing the selected phenol or 1-naphthol with phthalic or naphthalic acid, their anhydrides or acid chlorides at elevated temperature in the presence of a suitable catalyst, for example, zinc chloride or sulfuric acid to yield the corresponding symmetrical, i.e., bis-phenol or bis-naphthol phthalide or naphthalide. Unsymmetrical phthaleins and mixed phthalein indicator dyes, such as, benzene-resorcinol phthalide are prepared in a similar manner by condensing an o-aroyl benzoic acid dye intermediate with the selected phenol also in the presence of a suitable catalyst, such as, sulfuric acid at elevated temperature.

The present invention is concerned with a new method of synthesizing certain phthalein indicator dyes, namely, 1-naphthol phthalides and naphthalides.

SUMMARY OF THE INVENTION

It is, therefore, the primary object of the present invention to provide a novel method of synthesizing indicator dyes.

It is another object of the present inventon to provide a method of synthesizing 1-naphthol phthalides and naphthalides which may be symmetrical, unsymmetrical or mixed indicator dyes.

It is a further object of the present invention to provide novel intermediates useful in the preparation of such dyes.

Other objects of this invention will in part be obvious and will in part appear hereinafter.

The invention accordingly comprises the process involving the several steps and the relation and order of one or more of such steps with respect to each of the others and the product possessing the features, properties and the relation of elements which are exemplified in the following detailed disclosure and the scope of the application of which will be indicated in the claims.

According to the present invention, a method of preparing indicator dyes is provided wherein (a) a p-(na)phthalidylnaphthol is reacted with (b) a compound selected from a 1-naphthol and an indole in the presence of base to form a leuco dye intermediate which is then oxidized to form the corresponding 3,3-disubstituted (na)phthalide. The expressions "(na)phthalidyl" and "(na)phthalide" as used herein are intended to denote either the phthalidyl-substituted naphthol and the phthalide dye obtained therefrom or the naphthalidyl-substituted naphthol and the naphthalide dye obtained therefrom depending upon the para substituent of the naphthol reactant (a).

Because the reaction conditions are milder than those normally encountered in prior art procedures, the present method allows greater latitude in the selection of 1-naphthol reactants. For example, the more sensitive naphthol compounds, such as, those containing carboxy substituents may be employed as the (a) and/or (b) reactant without the loss of the carboxy group(s) and the formation of substantial amounts of decarboxylated by-products that usually occurs under Friedel-Crafts conditions. Since the present method is not limited to the more stable compounds, it allows greater latitude in the dyes that may be produced which includes not only symmetrical or bis naphthol (na)phthalides but unsymmetrical and mixed indicator dyes as well.

For a fuller understanding of the nature and objects of the present invention reference should be had to the following detailed description.

DESCRIPTION OF THE PREFERRED EMBODIMENTS

According to the present invention, it has been found that a second mole of a 1-naphthol or a mole of indole may be added to the 1:1 adduct of a 1-naphthol and a (na)phthalaldehydic acid and that the leuco dye intermediate thus obtained may be oxidized to yield the corresponding (na)phthalide indicator dye. Because - naphthols are not strongly nucleophilic in nature, the base-catalyzed addition of a second mole of naphthol to a p-(na)phthalidyl naphthol is quite unexpected. Moreover, 1-naphthol indicator dyes wherein both naphthyl radicals possess carboxy substituents may be produced in this manner without any substantial amount of decarboxylation as normally encountered in prior processes.

In one embodiment, the method of the present invention comprises:

1. reacting (a) a compound of the formula:

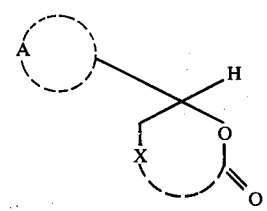

wherein A represents a 4'-hydroxy-1'-naphthyl radical and X represents the atoms necessary to complete a ring-closing moiety selected from a phthalide and preferably, a naphthalide and (b) a compound selected from a 1-naphthol having a free para position and an indole having a free 3-position in the presence of base to form a leuco dye intermediate of the formula

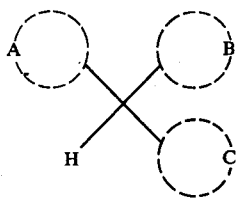

wherein B is a radical selected from 4'-hydroxy-1'-naphthyl and indol-3-yl; C is a radical selected from 8-carboxy-1-naphthyl and 2-carboxy-1-phenyl; and A has the same meaning given above; and 2. treating said leuco dye intermediate with an oxidizing agent to form the corresponding indicator dye having the formula:

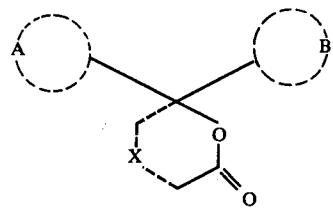

wherein A, B and X have the same meaning given above.

In another embodiment of the present invention, compound (a) in step (1) above is prepared by reacting a 1-naphthol and a (na)phthalaldehydic acid in the presence of an acid catalyst.

In a preferred embodiment of the present invention, 3,3-disubstituted phthalides and naphthalides are produced wherein the 3,3 substituents are 3'-carboxy-4'-hydroxy-1'-naphthyl radicals, the same or different. In this embodiment, the naphtholic —OH groups of the leuco dye intermediate preferably are ionized prior to oxidation of the intermediate to form the indicator dye product.

The reaction scheme of the present method is illustrated below wherein B'-H represents the 1-naphthol or indole which ultimately comprises the B radical in the final dye; C represents a 2-carboxy-1-phenyl radical

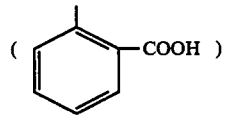

or an 1-naphthyl radical

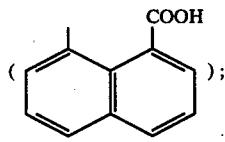

and X represents the atoms necessary to complete a phthalide or naphthalide ring-closing moiety. Step (1a) represents the additional ionization step in the production of carboxy-naphthol dyes wherein the p-(na)phthalidyl naphthol contains a carboxy group ortho to the naphtholic —OH and B'—H comprises a 1-naphthol also containing a carboxy group ortho to the naphtholic —OH.

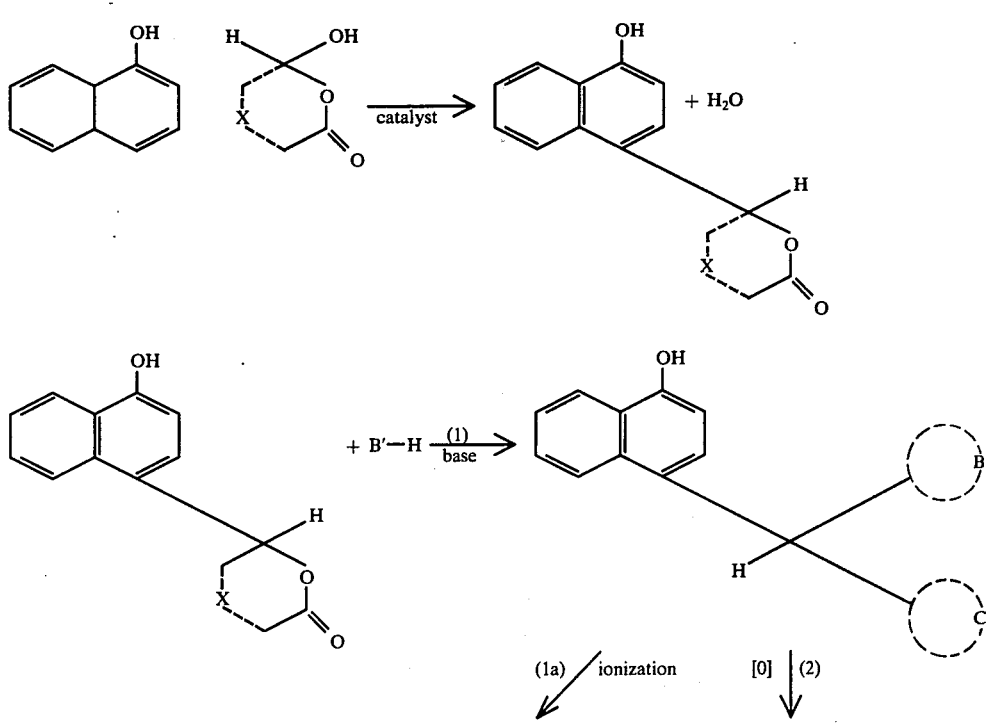

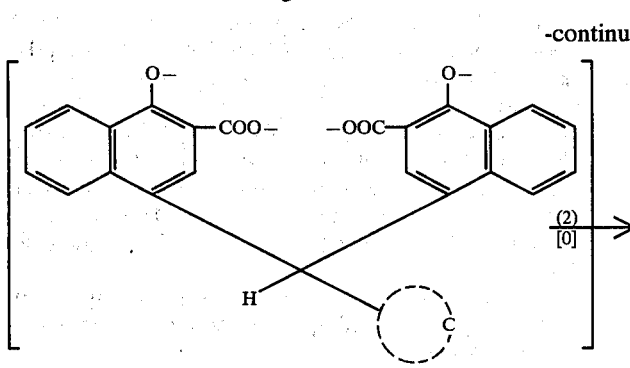
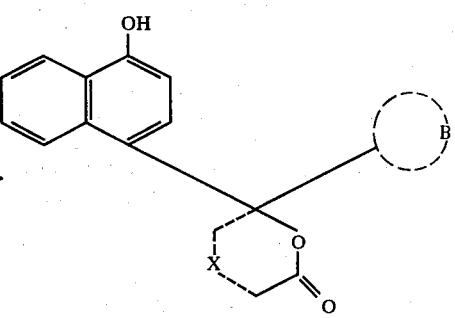

Typical of the indicator dyes that may be prepared according to the present invention are those represented by the formula:

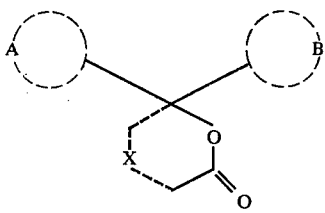

(I)

wherein A represents a 4'-hydroxy-1'-naphthyl radical; B represents a radical selected from 4'-hydroxy-1'-naphthyl and indol-3-yl; and X represents the atoms necessary to complete a ring-closing moiety selected from a phthalide and a naphthalide.

The indicator dyes represented above may contain one or more substituents in addition to those specified as may be readily selected by those skilled in the art to achieve certain desired properties. Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as, phenyl, 2-hydroxyphenyl, 2-hydroxy-4-dodecyloxyphenyl, and naphthyl; alkaryl, such as, benzyl, phenethyl, phenylhexyl, p-octylphenyl, p-dodecylphenyl; alkoxy, such as, methoxy, ethoxy, butoxy, 1-ethoxy-2-($\beta$-ethoxyethoxy), dodecyloxy and octadecyloxy; aryloxy, such as, phenoxy, benzyloxy, naphthoxy; alkoxyalkyl, such as methoxyethyl, dodecyloxyethyl; halo, such as, fluoro, bromo, and chloro; trifluoralkyl, such as, trifluoromethyl, mono- and bis-trifluoromethyl carbinol; sulfonamido; sulfamoyl; acyl and its derivatives; aminomethyl; amido; sulfonyl; sulfo; cyano; nitro; amino including mono- and disubstituted amino, e.g., N-ethyl amino and N,N'-dimethylamino; carboxy; and hydroxyl.

As mentioned previously, the indicator dyes produced in accordance with the present invention may be symmetrical in which instance the B radical would be a naphthol radical identical to A, or they may be unsymmetrical or mixed indicators. When unsymmetrical, the A radical and B radical both would be derived from a 1-naphthol, but each radical would contain different substituents or the same substituents in different positions or one radical would be substituted and the other unsubstituted. The term "mixed indicator" is intended to denote indicator dyes where the A radical and B radical are derived from different aromatic compounds, and in this instance, one from naphthol and the other from indole.

For use as optical filter agents in photographic processes, such as, diffusion transfer processes employing highly alkaline processing solutions, it may be desirable that the indicator dye selected as the optical filter agent possess a relatively high pKa so that the dye will be in a light-absorbing form during the initial stages of processing and yet may be rendered substantially non-light absorbing within a relatively brief interval as the pH subsequent to substantial image formation is reduced in order to permit early viewing of the image. Such dyes may be prepared according to the present invention by appropriate selection of the reactants to provide in the final dye, an A and/or B radical possessing a hydrogen-bonding group adjacent to the functional —OH of the naphthol radical or adjacent to the —NH— of the indole radical. For example, indicator dyes of Formula I above wherein the A radical possesses a hydrogen-bonding group substituted on the carbon atom ortho to the naphtholic —OH possess a relatively high pKa which makes them useful as optical filter agents in the aforementioned processes.

The association of two atoms through hydrogen to form a hydrogen bond between or within molecules is well known. When hydrogen is attached to an electronegative atom, for example, O or N, the resultant bond is polarized. If directed toward another atom (M) with an unshared pair of electrons, the hydrogen acts as a bridge between the atoms (O-H . . . M) due to the electrostatic attraction to both atoms between which the hydrogen proton can be transferred. In the compounds noted above, an intramolecular hydrogen bond is formed between the p-OH (or the —NH—) and the adjacent hydrogen-bonding group, e.g., between the naphtholic —OH and a group containing a heteroatom possessing an active unshared pair of electrons, such as, O, N, S or halogen, e.g., F., which has a free electron pair or a negative charge in basic solution and which preferably is capable of forming a 5-, 6- or 7-membered and particularly a 5- or 6-membered hydrogen bonded ring with the functional, i.e., naphtholic —OH. Preferably, the heteroatom in the hydrogen-bonding group has attached to it a proton which is more acidic than the proton on the naphtholic —OH and ionizes in basic solution a negative charge. Such groups include, for example, carboxy; hydroxy; o-hydroxyphenyl; bis trifluoromethyl carbinol; sulfonamido (—NH—SO$_2$—R') and sulfamoyl (—SO$_2$—NH—R"). R' and R" usually contain up to about 20 carbon atoms and may be alkyl, aryl, aralkyl and alkaryl. Typical R' and R" substituents include branched or straight chain alkyl, e.g., methyl, ethyl, isopropyl, n-butyl, t-butyl, hexyl, octyl, dodecyl, hexadecyl, octadecyl and eicosanyl; aryl, e.g., phenyl and naphthyl; and aralkyl and alkaryl, particularly phenyl-substituted alkyl and alkyl-substituted phenyl, e.g., benzyl, phenethyl, phenylhexyl, phenyldodecyl, p-methylphenyl, p-hexylphenyl, p-octylphenyl and p-dodecylphenyl.

Naphthol indicator dyes which are particularly useful as optical filter agents in diffusion transfer photographic processes are those wherein at least one and preferably both of the naphthol radicals possess a carboxy group adjacent to the naphtholic —OH as produced in accordance with the preferred embodiment of the present method. Since naphthol naphthaleins have a higher pKa than the corresponding naphthol phthaleins, the carboxynaphthol naphthalides are particularly preferred for use in highly alkaline photographic processing compositions. For example, 3,3-bis(-3'-carboxy-4'-hydroxy-1'-naphthyl)phthalide has a pKa of approximately 12.5 whereas 3,3-bis(3'-carboxy-4'-hydroxy-1'-naphthyl)-naphthalide has a pKa of about 13.5. High pKa naphthol phthaleins and naphthaleins substituted with hydrogen-bonding groups including carboxy-naphthol indicator dyes form the subject matter of copending U.S. Pat. application Ser. No. 103,865 filed Jan. 4, 1971, now U.S. Pat. No. 3,833,614.

Specific examples of 1-naphthol indicator dyes that may be prepared according to the method of the present invention are as follows:

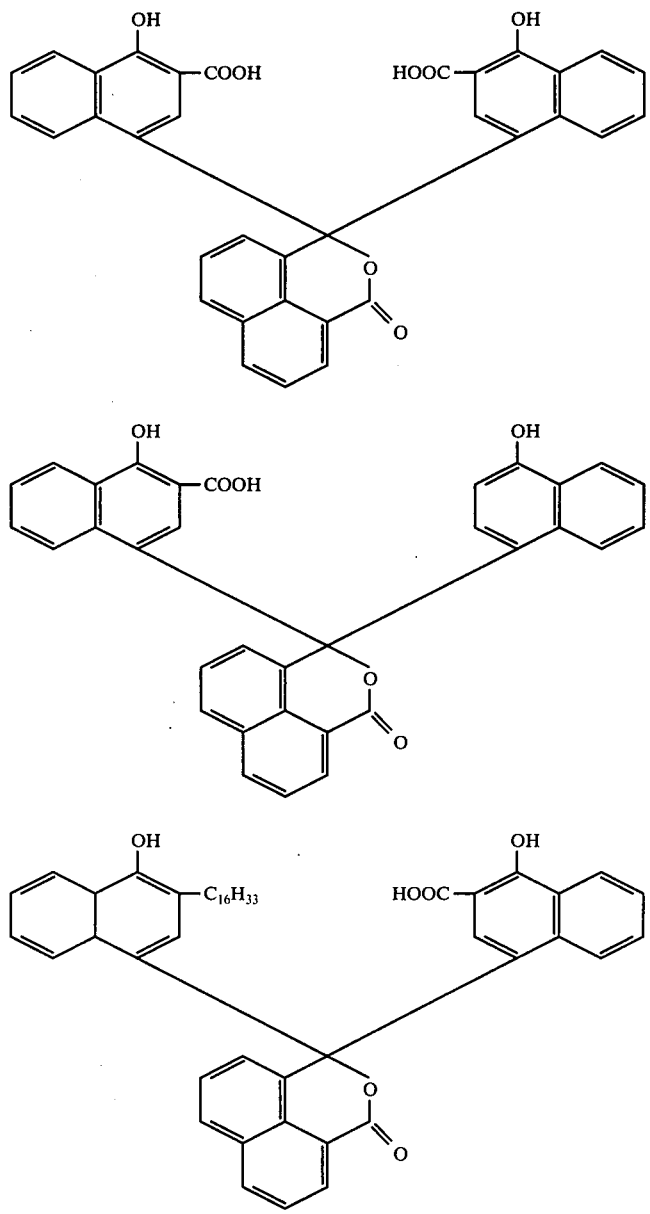

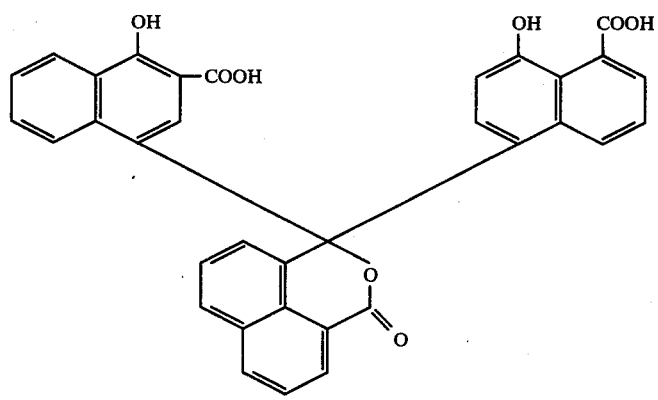
(4)
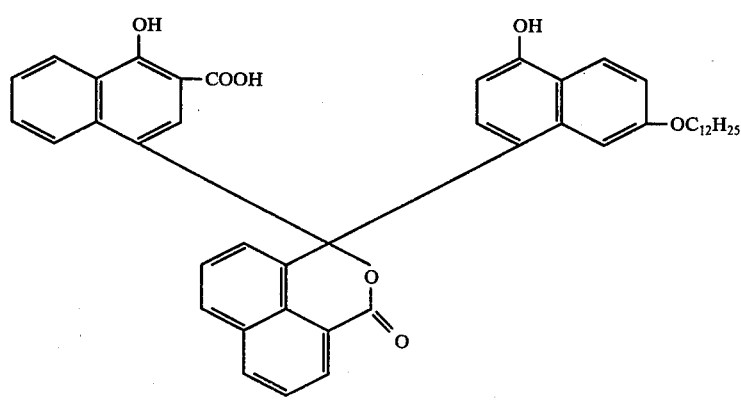
(5)
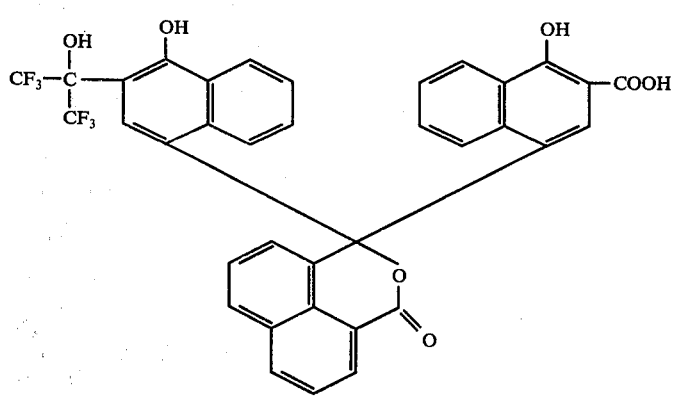
(6)
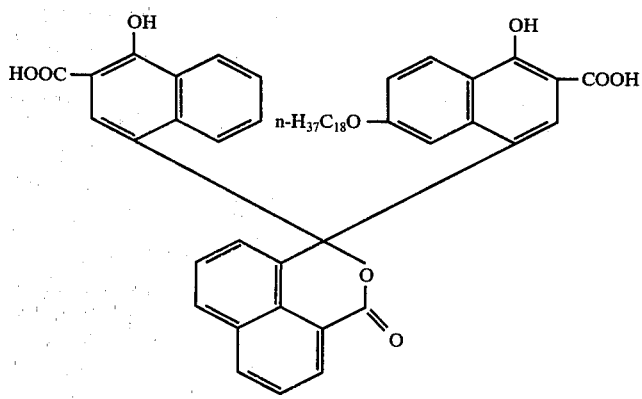
(7)

-continued
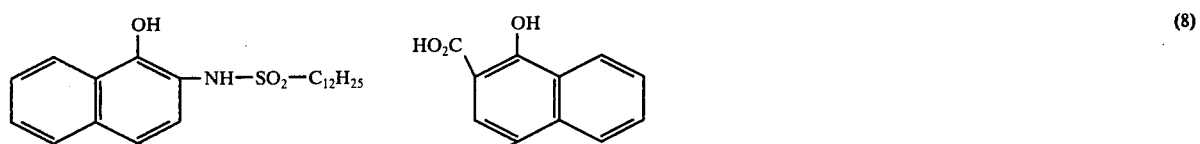
(8)
(9)
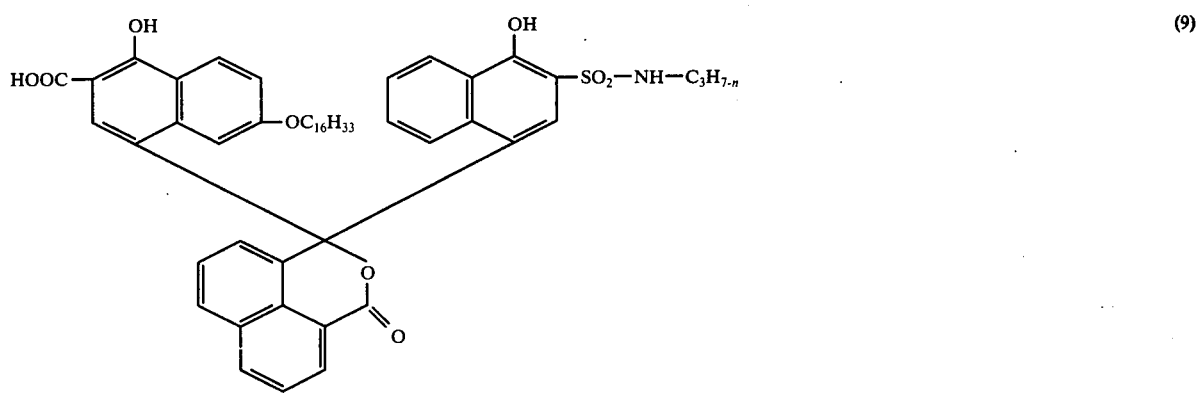
(10)
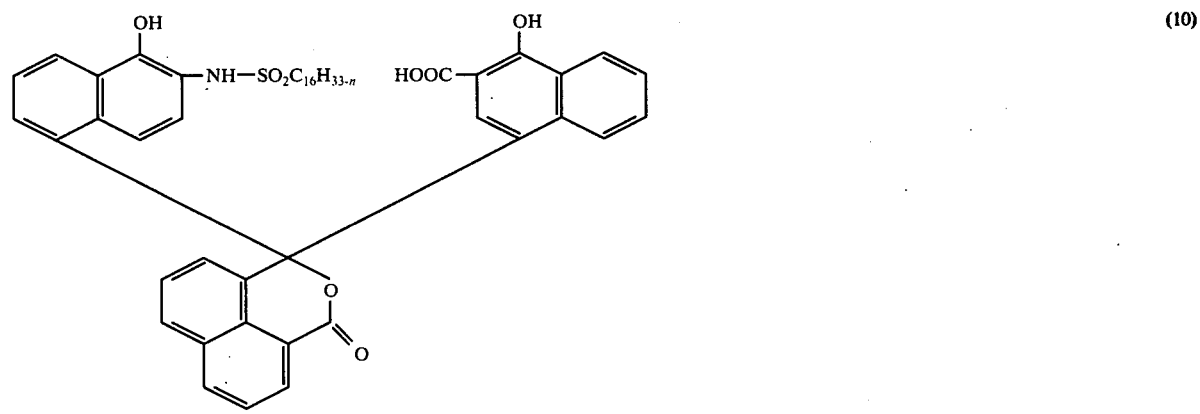
(11)
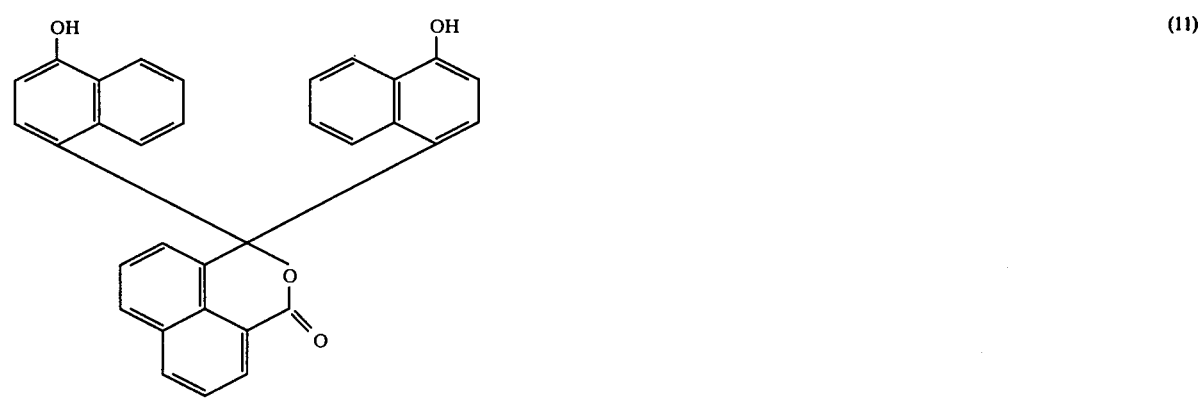

-continued
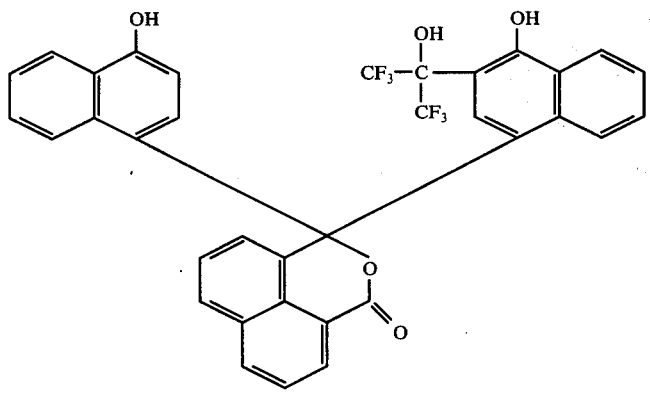 (12)
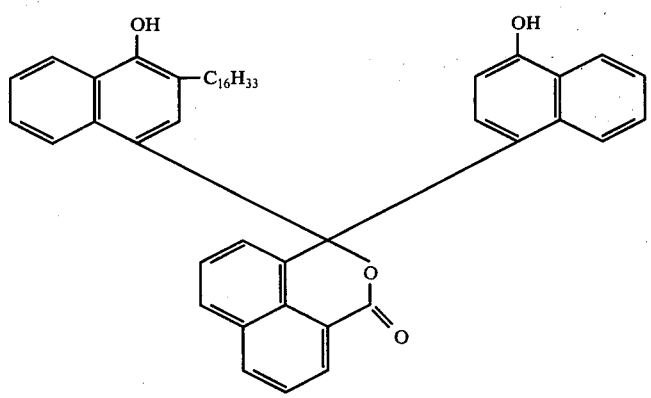 (13)
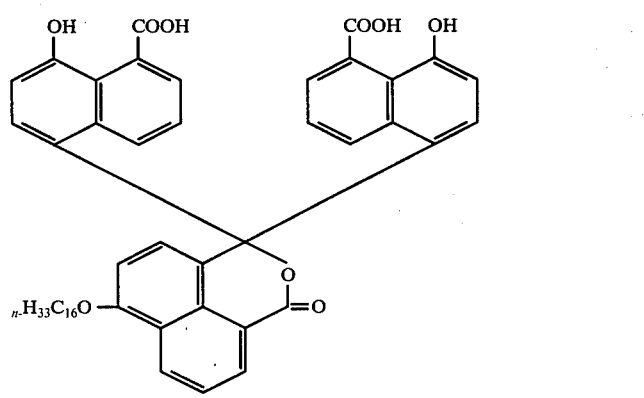 (14)
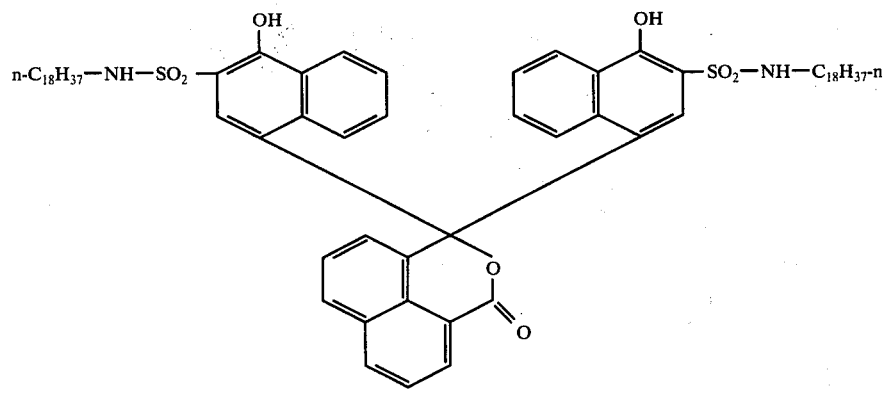 (15)

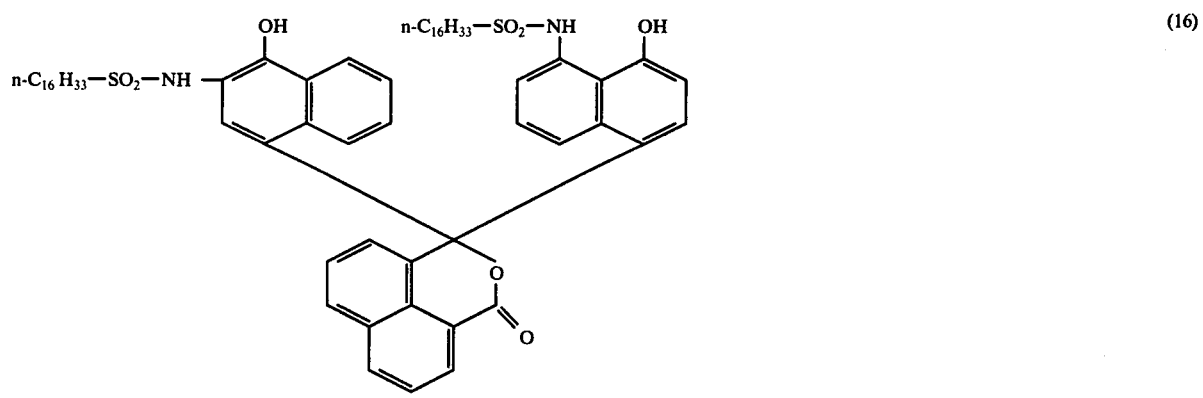
(16)
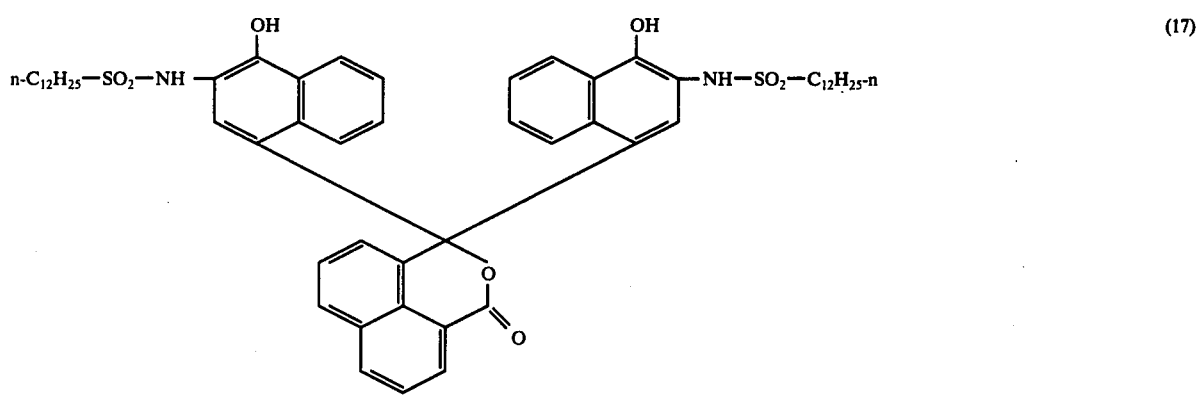
(17)
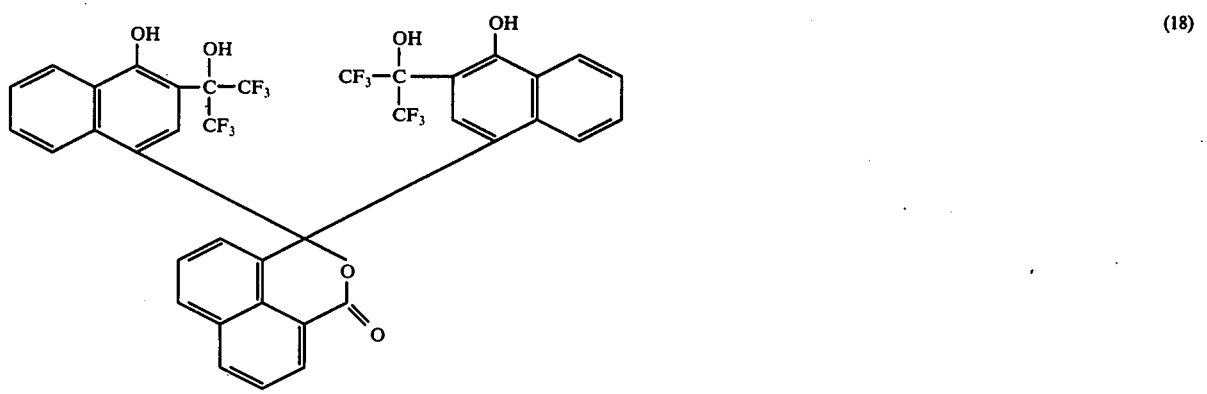
(18)
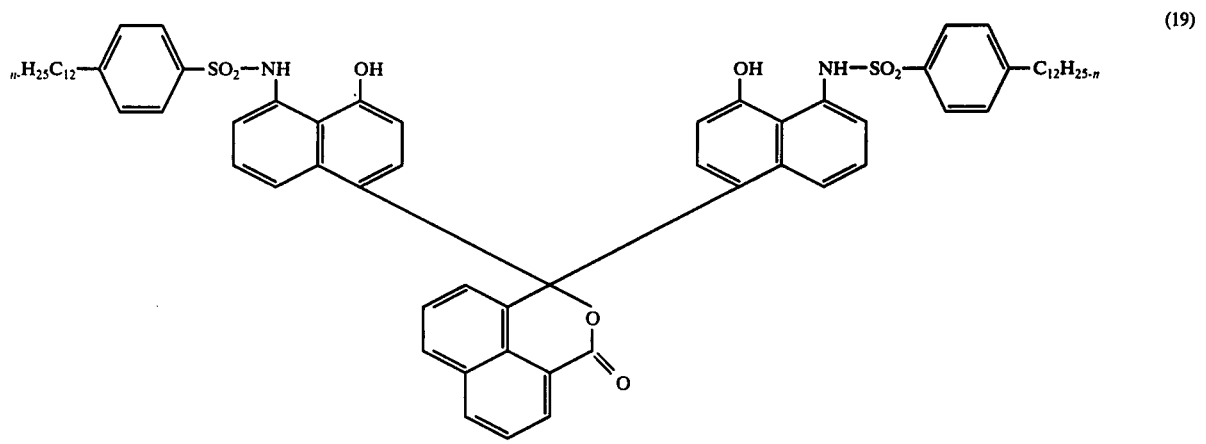
(19)

(20)
(21)
(22)
(23)

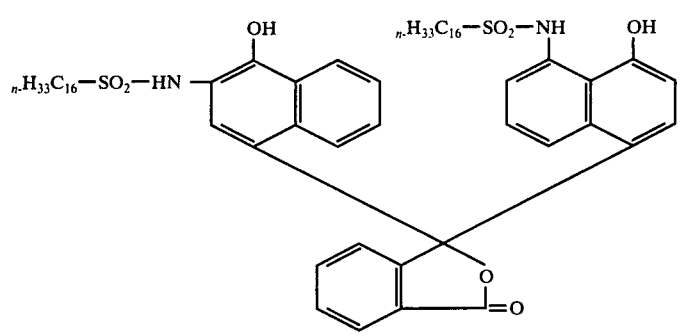
(24)
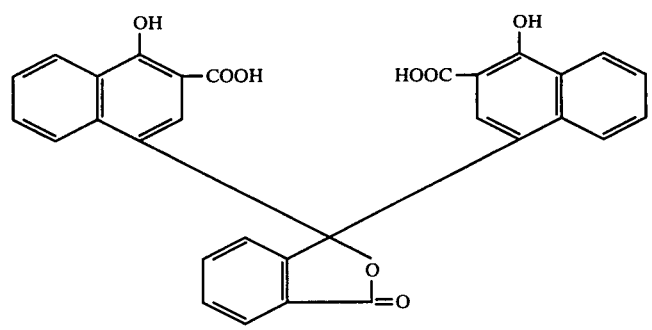
(25)
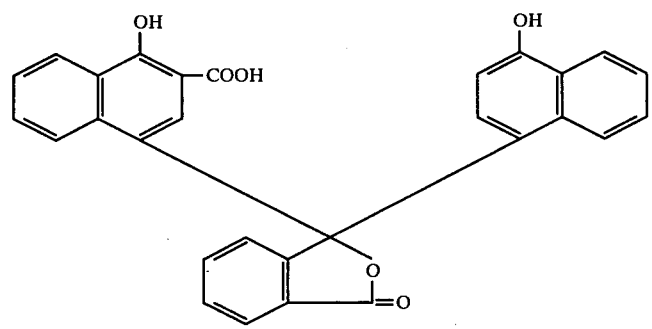
(26)
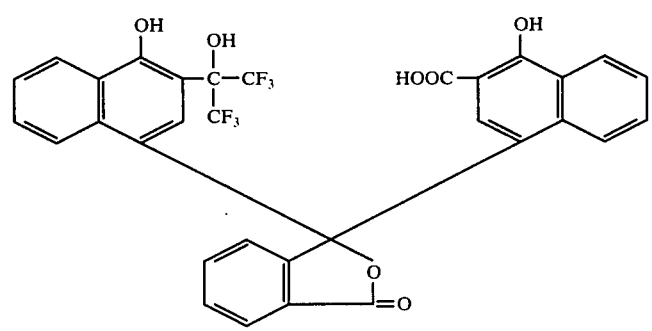
(27)
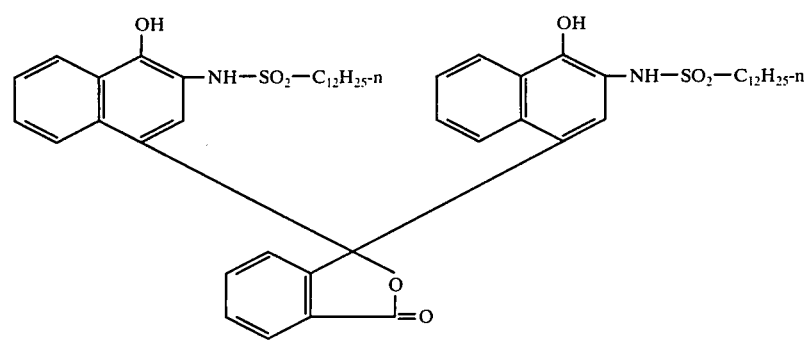
(28)

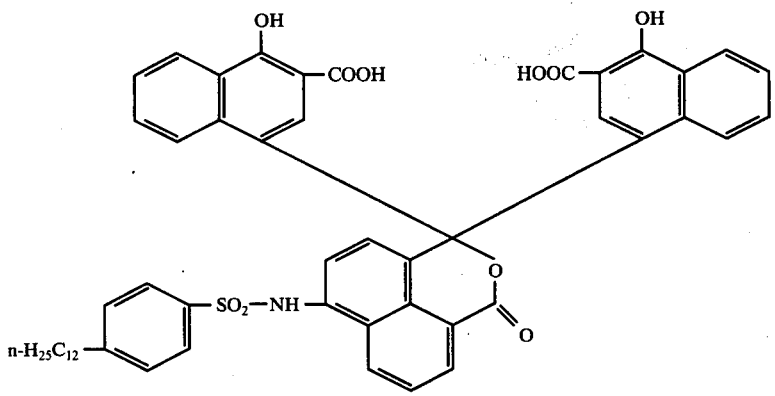
(29)
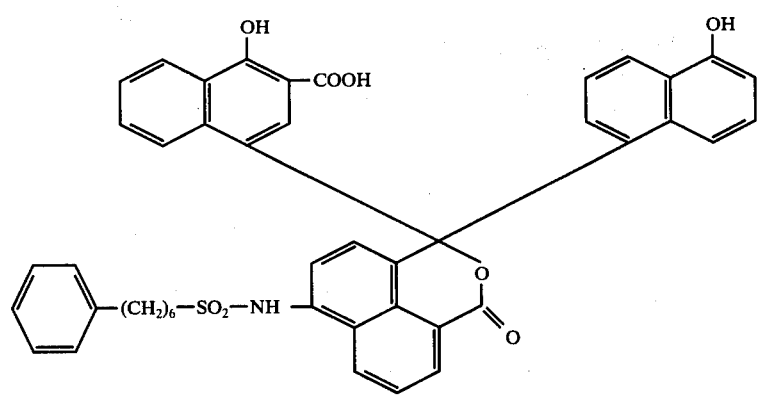
(30)
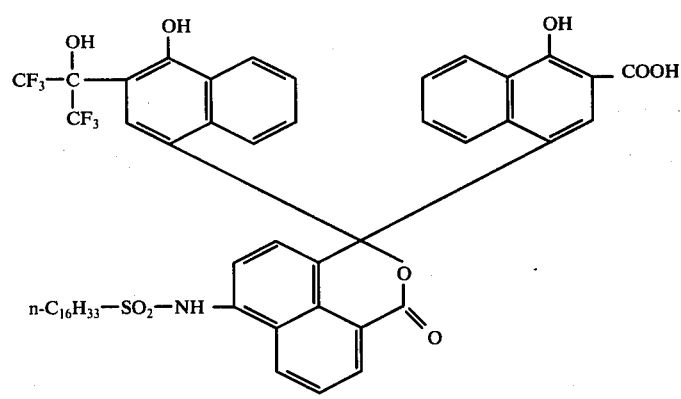
(31)
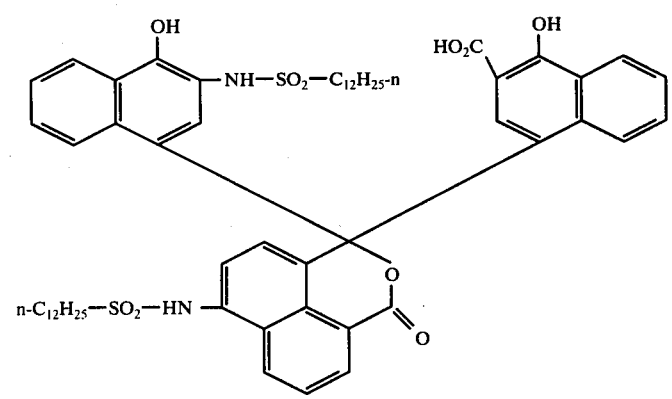
(32)

-continued
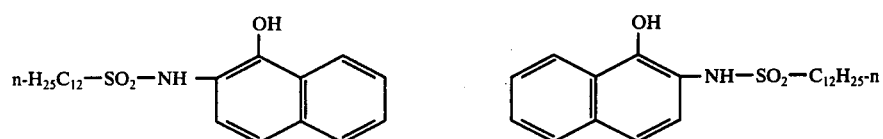 (33)
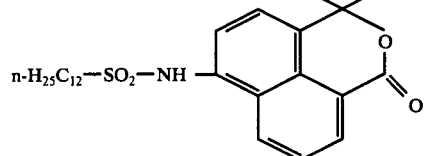
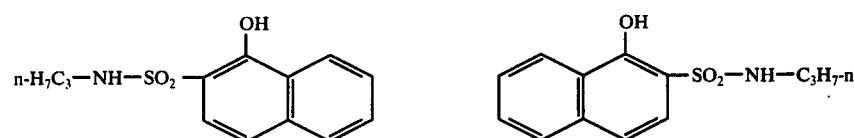 (34)
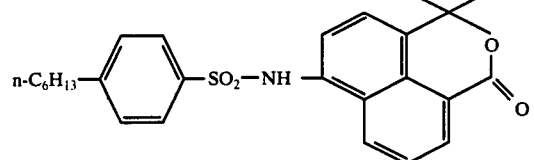
(35)
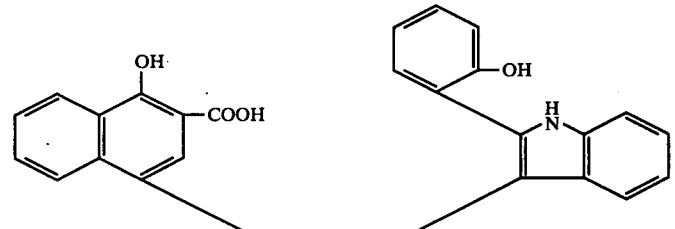
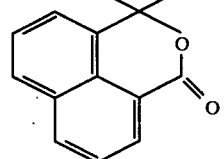
(36)
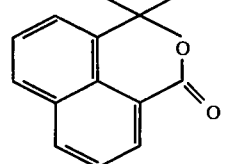

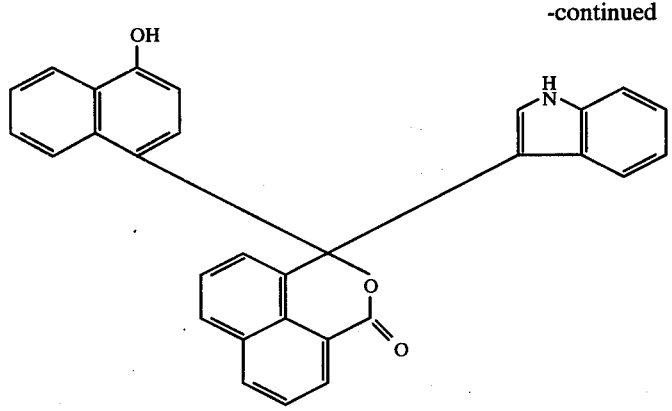
(37)
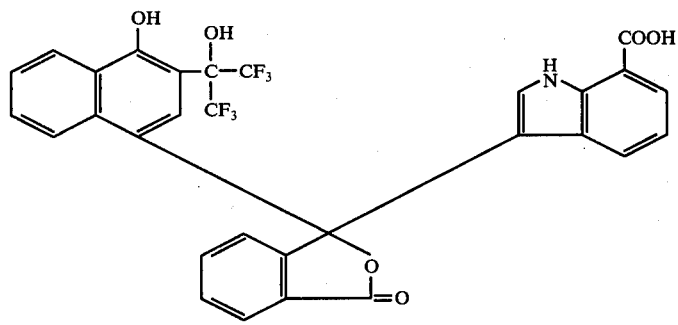
(38)
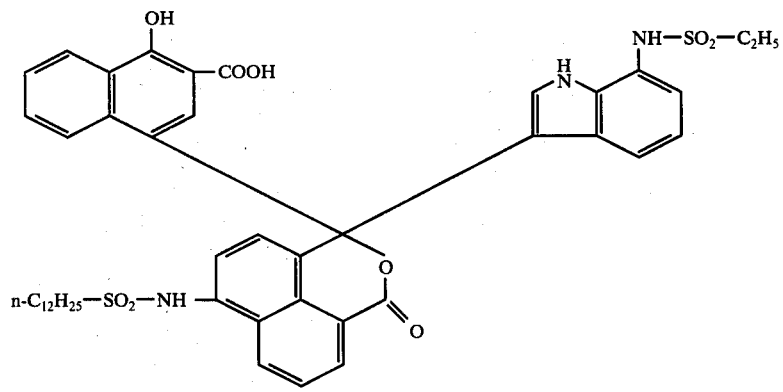
(39)
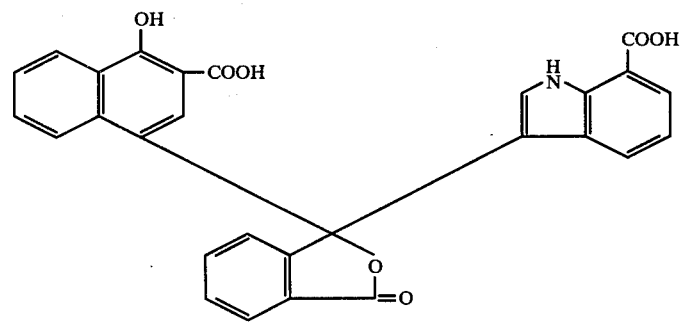
(40)
The novel intermediates of the present invention are the (na)phthalidylnaphthols obtained as the reaction product of a 1-naphthol and a (na)phthalaldehydic acid as represented in formula (II) and the leuco dye intermediates obtained as the reaction product of the (na)phthalidylnaphthol and a 1-naphthol or indole as represented in formula (III).
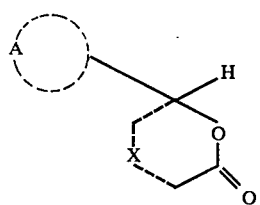
(II)

wherein A represents 4'-hydroxy-1'-naphthyl and X represents the atoms necessary to complete a ring-closing moiety selected from a phthalide and a naphthalide and preferably is naphthalide;

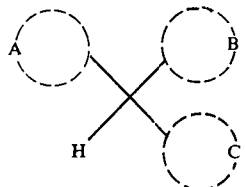

(III)

wherein A represents 4'-hydroxy-1'-naphthyl; B represents 4'-hydroxy-1'-naphthyl or indol-3-yl and C represents a 2-carboxy-1-phenyl radical or an 8-carboxy-1-naphthyl radical and preferably is 8-carboxy-1-naphthyl. It will be appreciated that the above intermediates may contain one or more substitutents as ultimately desired in the complete dye, such as those enumerated above.

In a preferred embodiment, the intermediates of the present invention possess naphthalide as the ring-closing moiety and comprise compounds as represented by the following formulas:

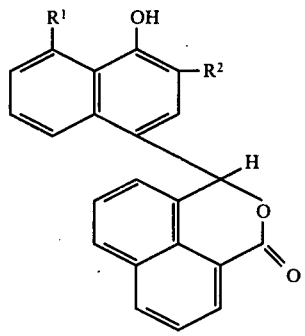

(IIa)

wherein $R^1$ and $R^2$ each are selected from hydrogen and a hydrogen-bonding group, at least one of $R^1$ and $R^2$ being hydrogen. Preferably, $R^1$ is hydrogen and $R^2$ is hydrogen or a hydrogen-bonding group selected from carboxy, hydroxy, o-hydroxyphenyl, bis trifluoromethyl carbinol, sulfonamido and sulfamoyl.

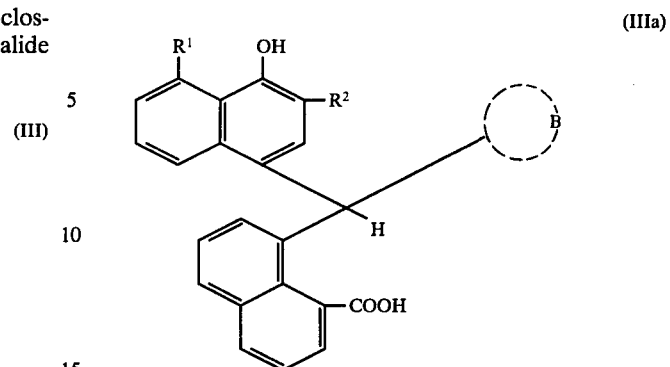

(IIIa)

wherein $R^1$ and $R^2$ each are selected from hydrogen and a hydrogen-bonding group, at least one of $R^1$ and $R^2$ being hydrogen. Preferably, $R^1$ is hydrogen and $R^2$ is hydrogen or a hydrogen-bonding group and B represents

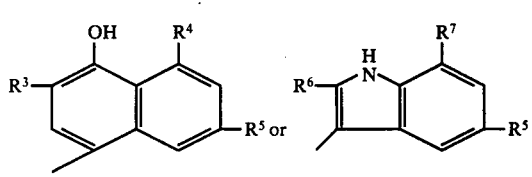

wherein $R^3$ and $R^4$ each are selected from hydrogen and a hydrogen-bonding group, at least one of $R^3$ and $R^4$ being hydrogen, $R^6$ and $R^7$ each are selected from hydrogen and a hydrogen-bonding group, at least one of $R^6$ and $R^7$ being hydrogen and $R^5$ is selected from hydrogen and alkoxy containing 1 to 18 carbon atoms. The hydrogen-bonding group preferably is selected from carboxy, hydroxy, o-hydroxyphenyl, bis trifluoromethyl carbinol, sulfonamido and sulfamoyl. Where it is desired to employ the above classes of intermediates in the preparation of indicator dyes having a relatively high pKa, $R^2$ of A is preferably a hydrogen-bonding group and for obtaining a further increase in the pKa of the indicator dye product, $R^3$ or $R^4$ of the 4'-hydroxynaphthyl radical B or $R^6$ or $R^7$ of the indolyl radical B is a hydrogen-bonding group.

Specific examples of the novel leuco dye intermediates of the present invention include:

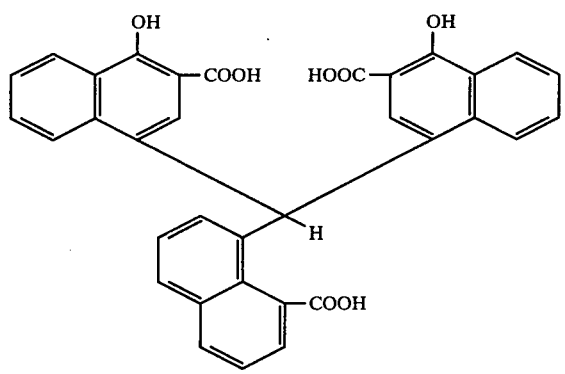

(41)

(42)

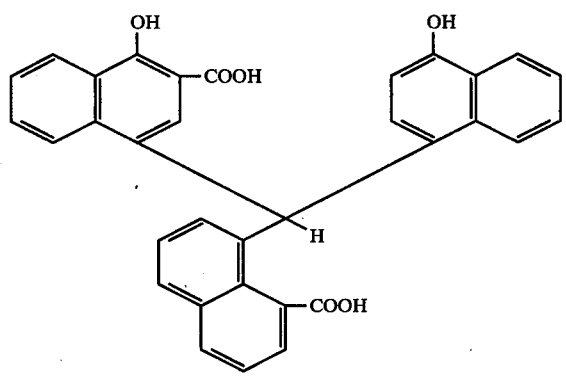
(43)
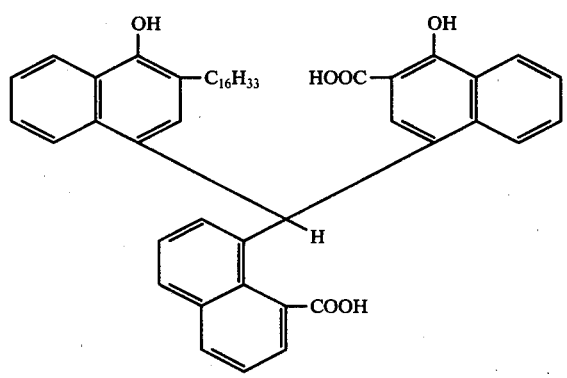
(44)
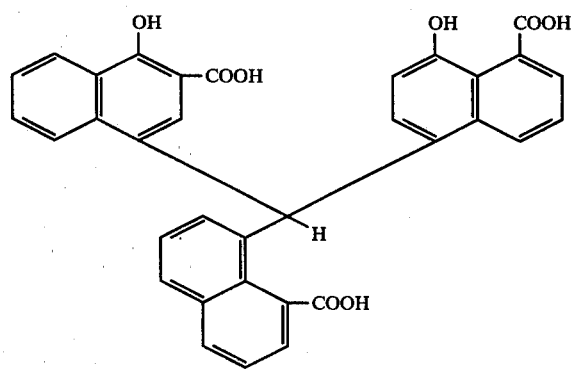
(45)
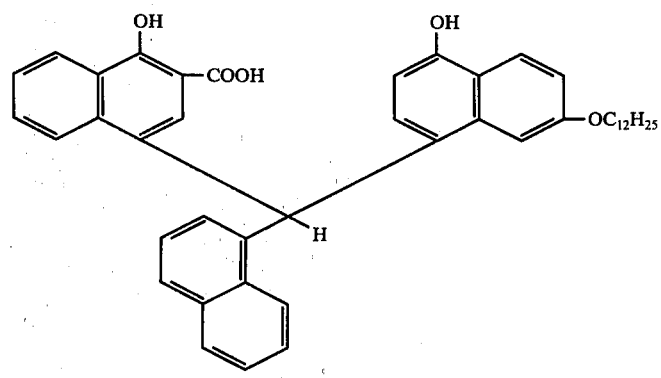
(46)

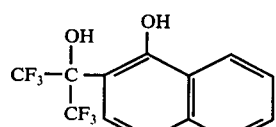 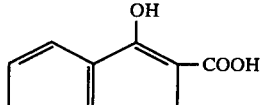
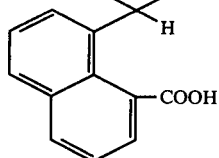
(47)
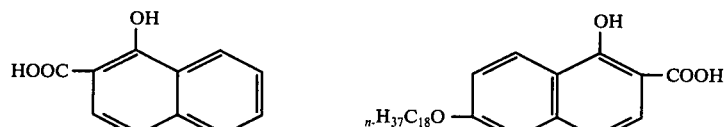
(48)
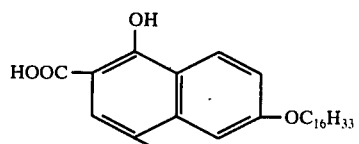 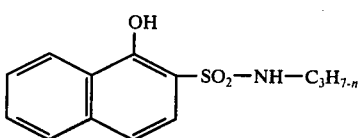
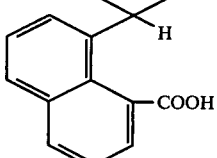
(49)
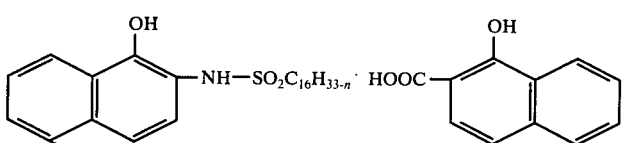
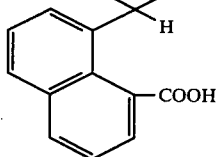
(50)
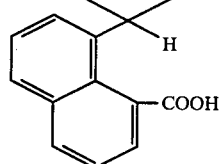

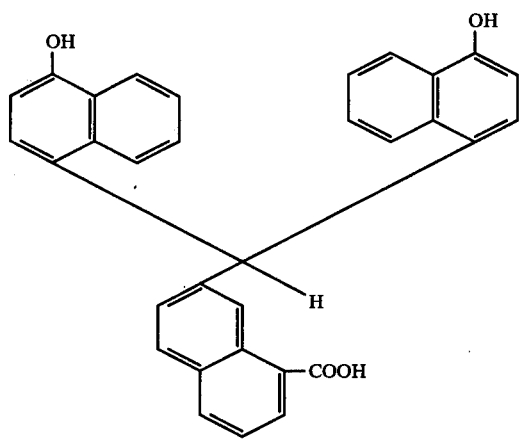
(51)
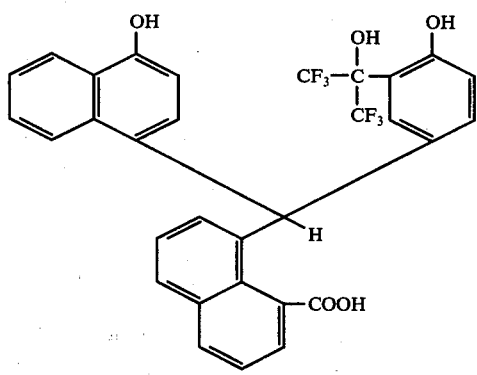
(52)
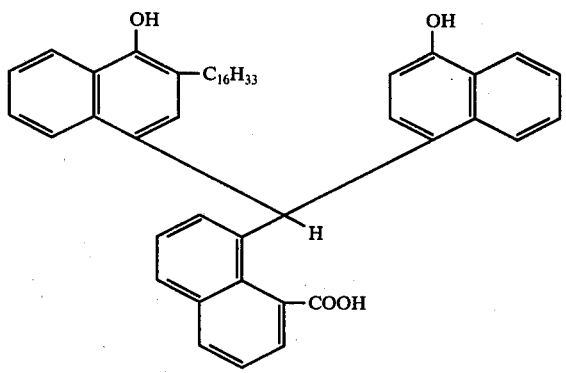
(53)
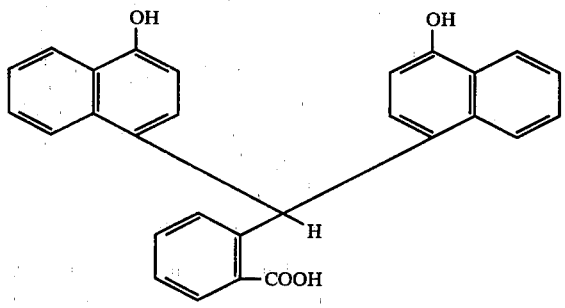
(54)

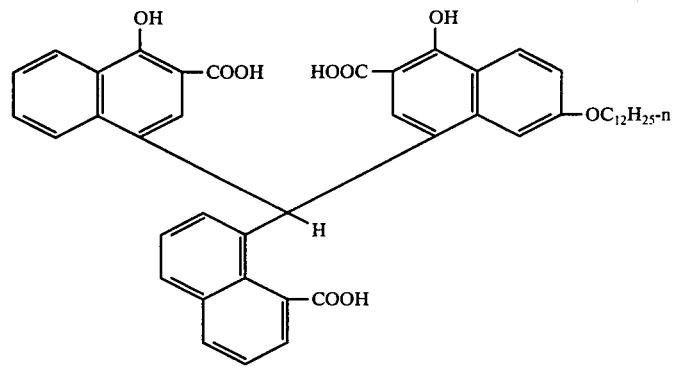
(55)
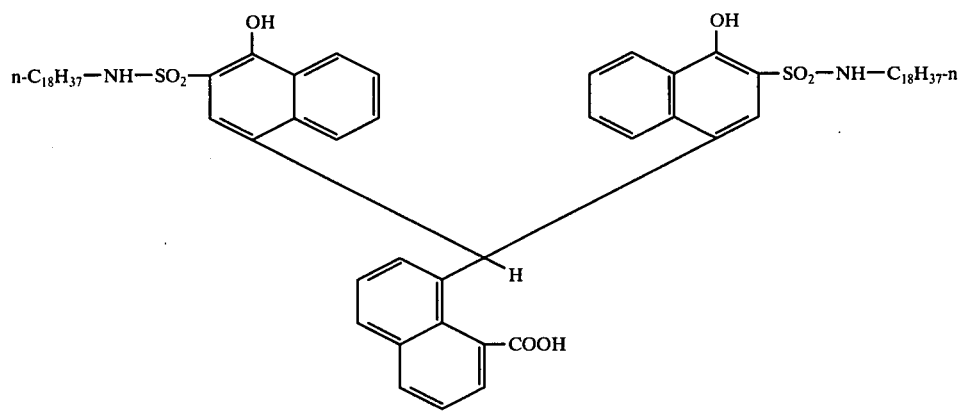
(56)
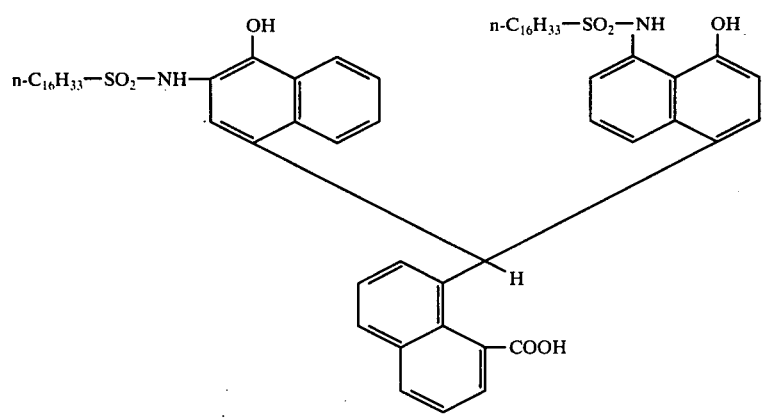
(57)
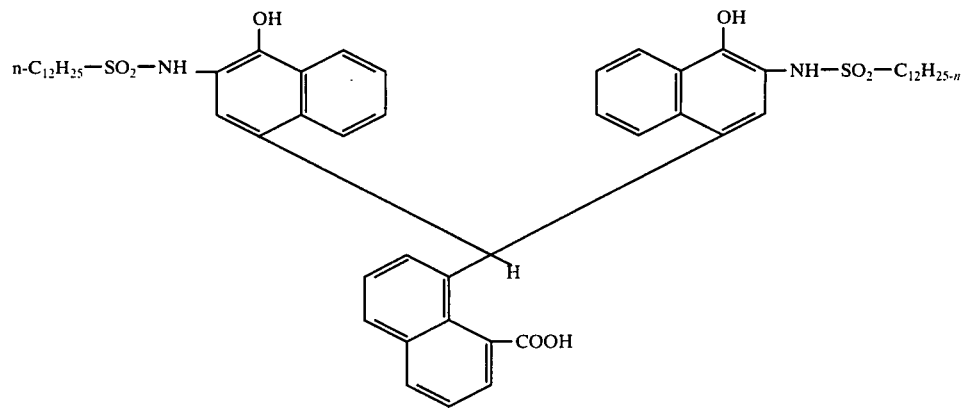
(58)

-continued
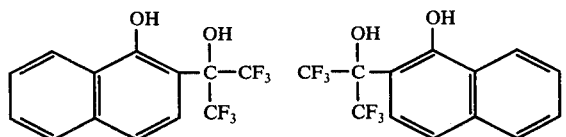
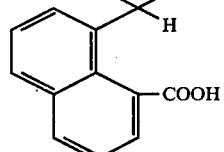
(59)
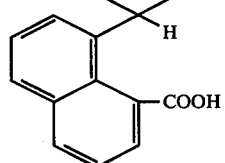
(60)
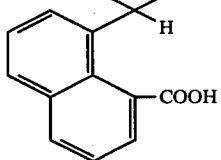
(61)
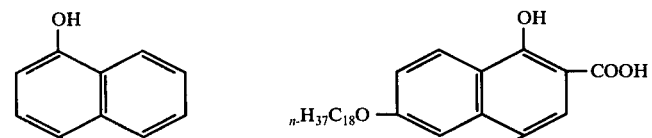
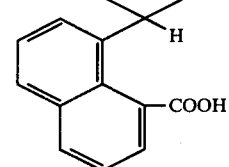
(62)

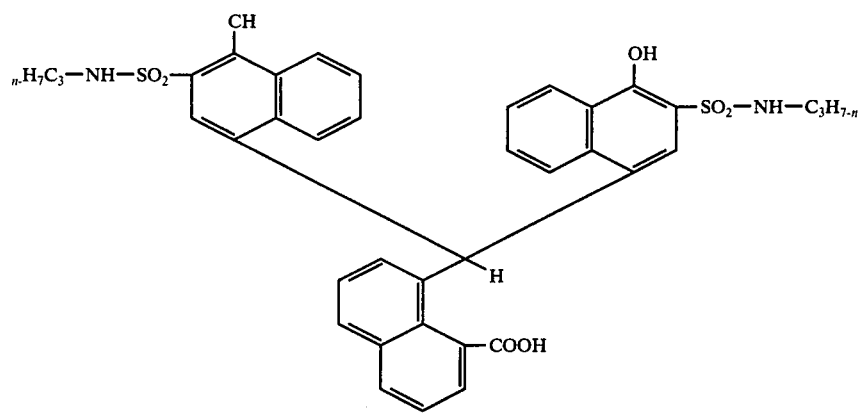
(63)
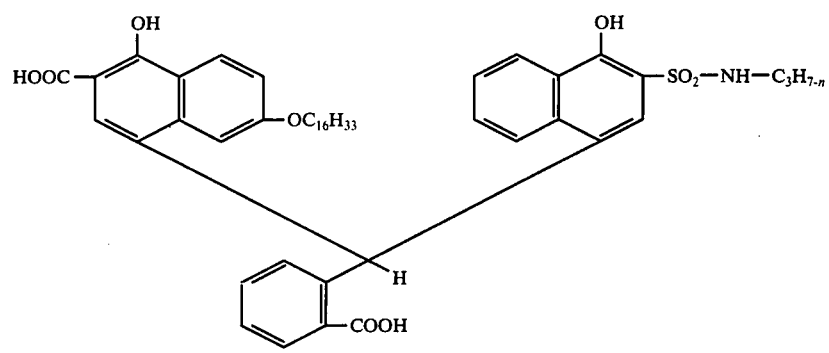
(64)
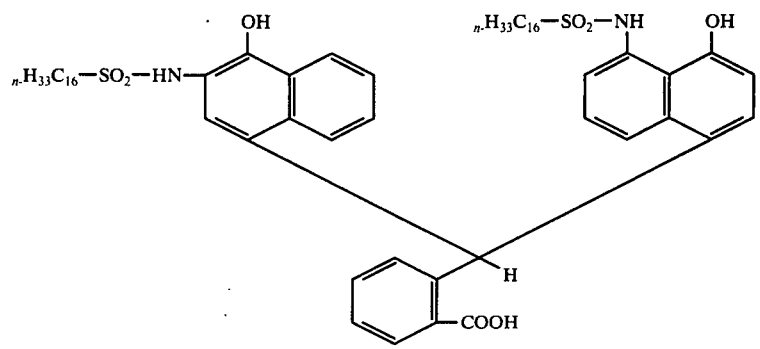
(65)
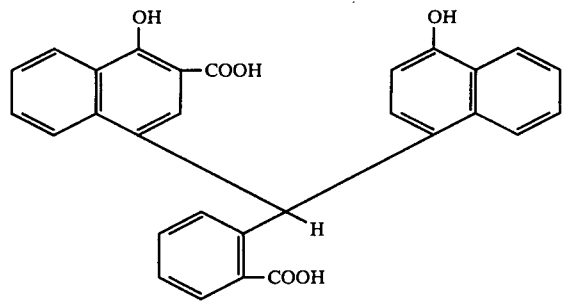
(66)

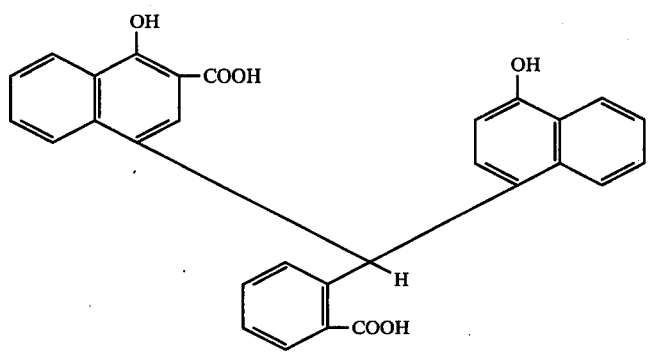
(67)
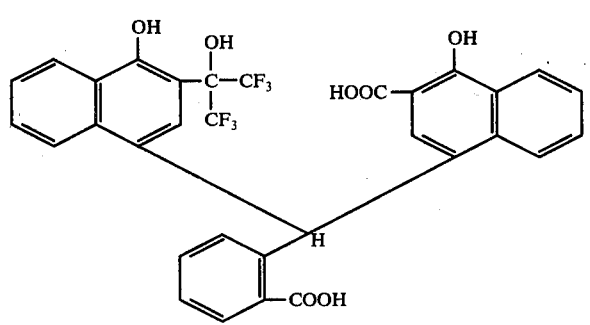
(68)
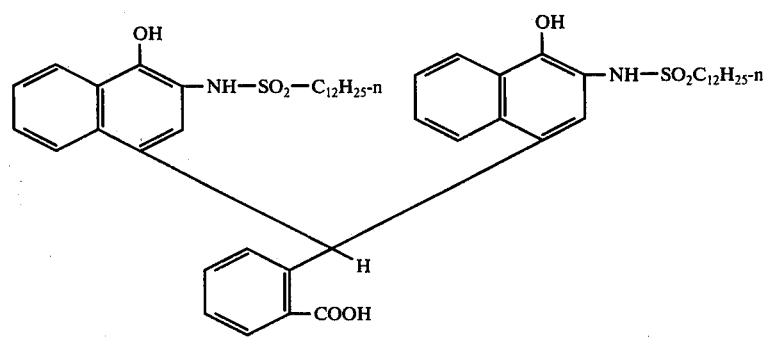
(69)
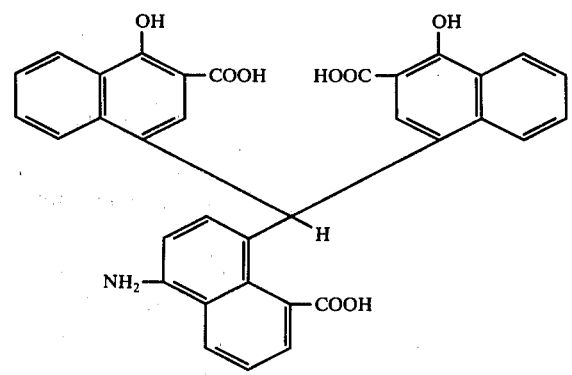
(70)

-continued
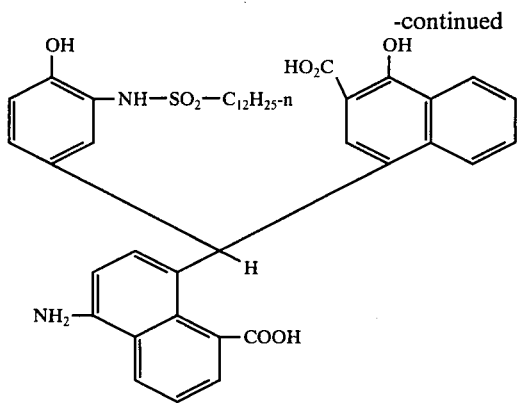
(71)
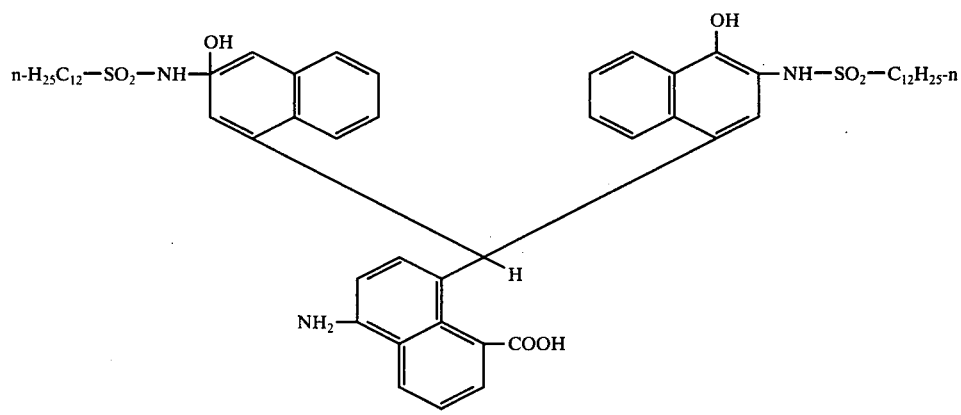
(72)
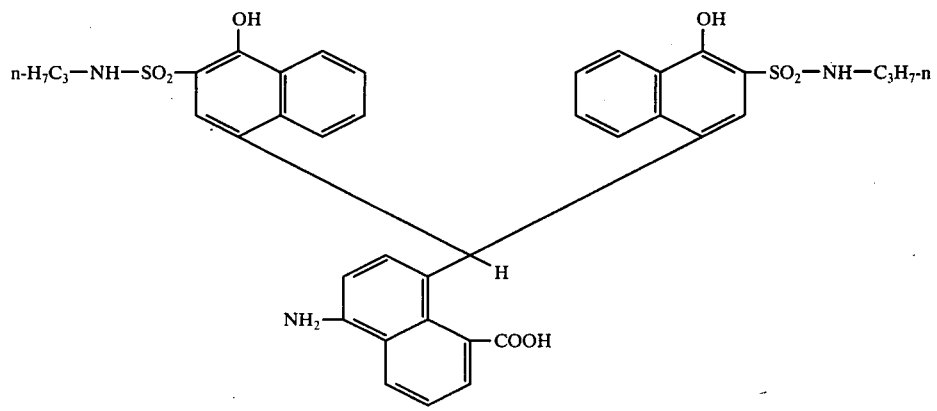
(73)
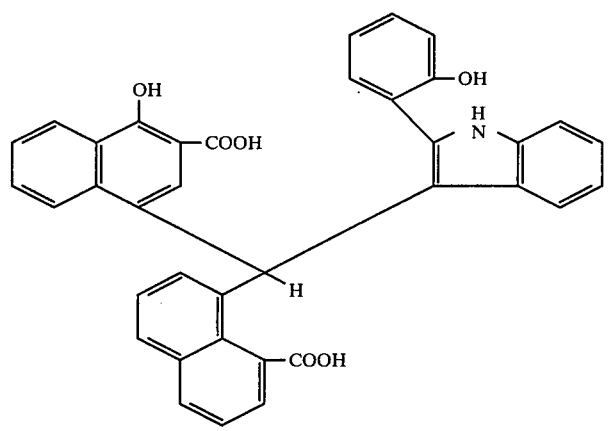
(74)

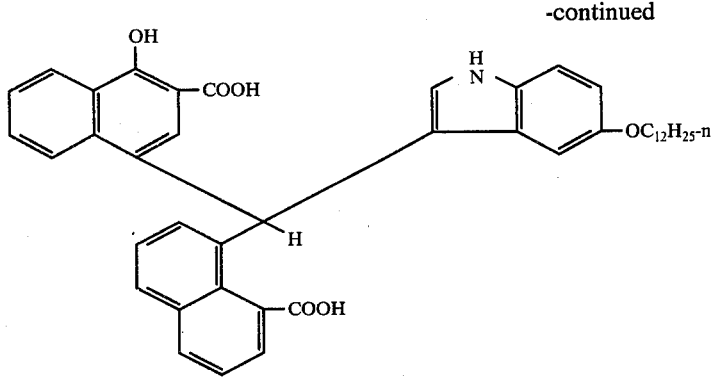
(75)
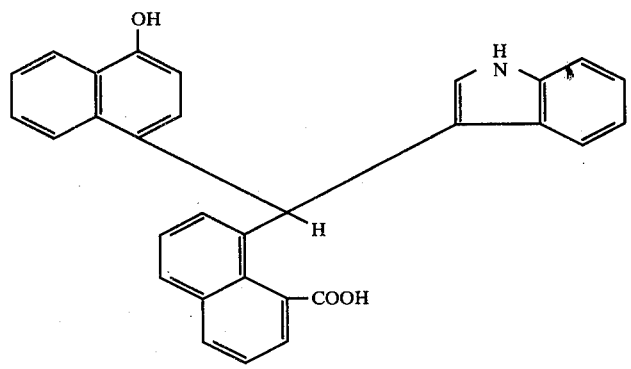
(76)
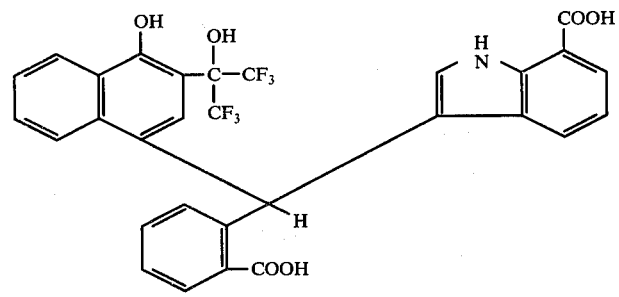
(77)
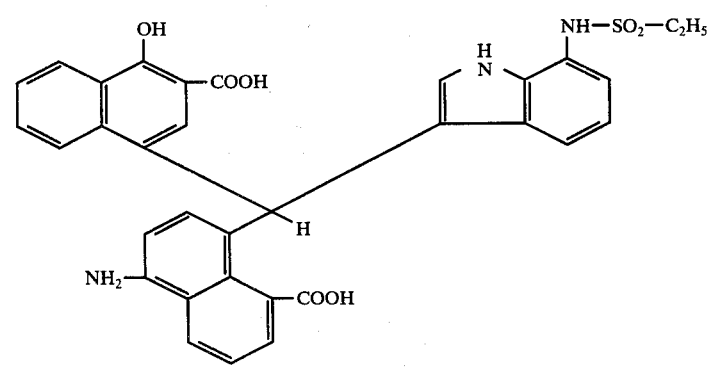
(78)
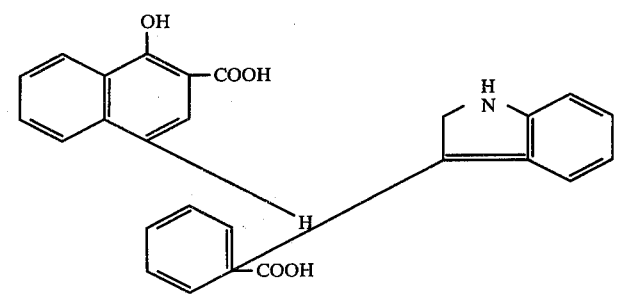

Specific examples of p-(na)phthalidyl intermediates of the present invention include:
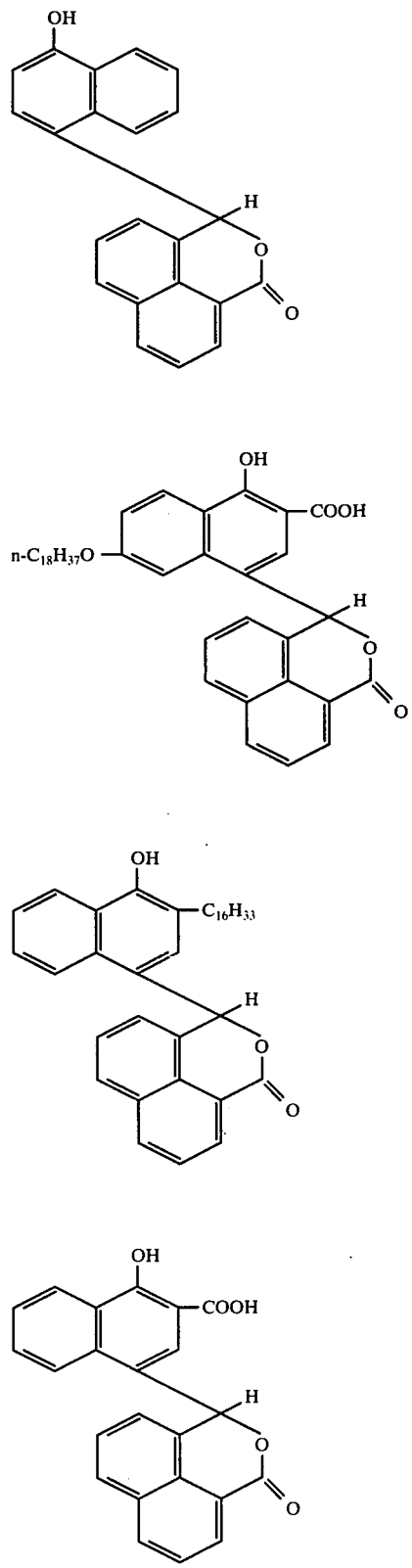
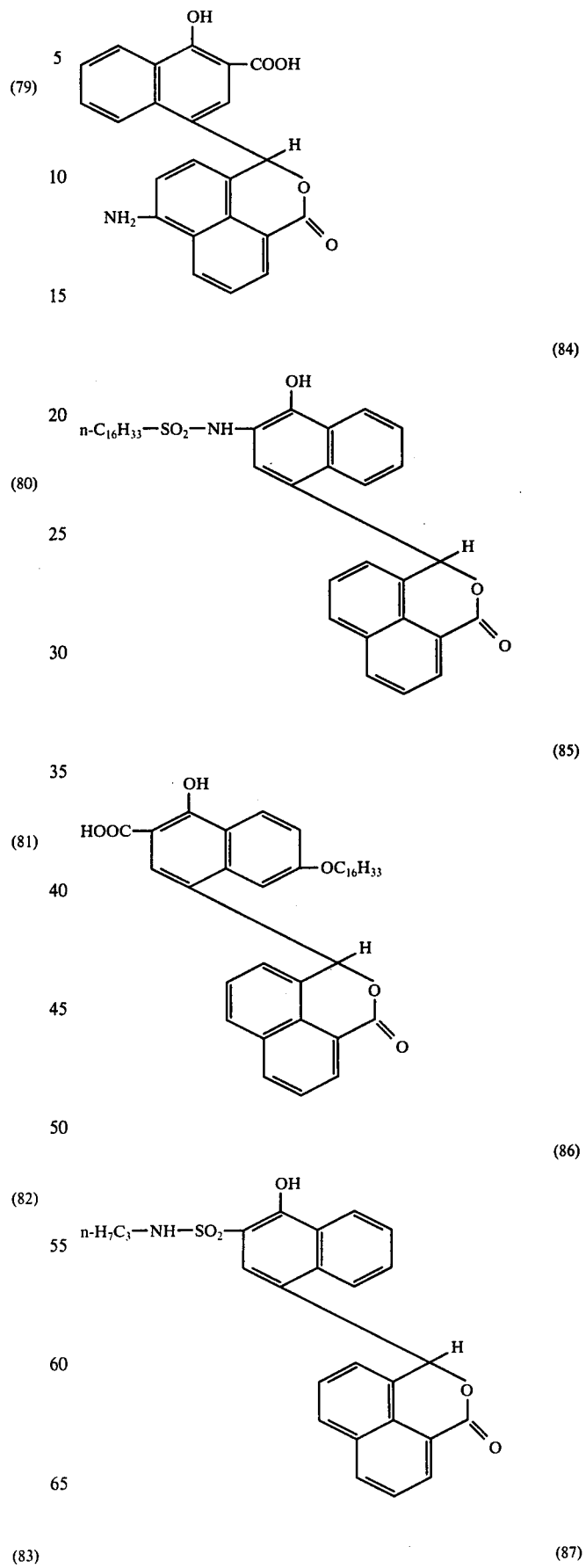

-continued

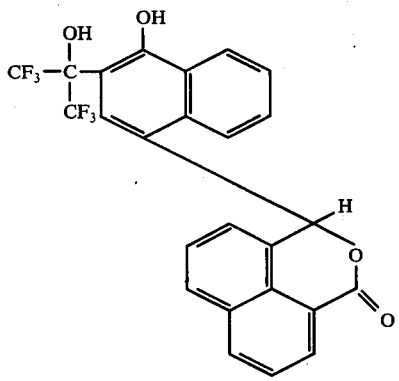

(88)

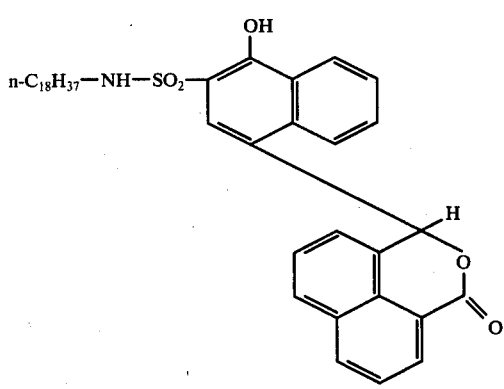

(89)

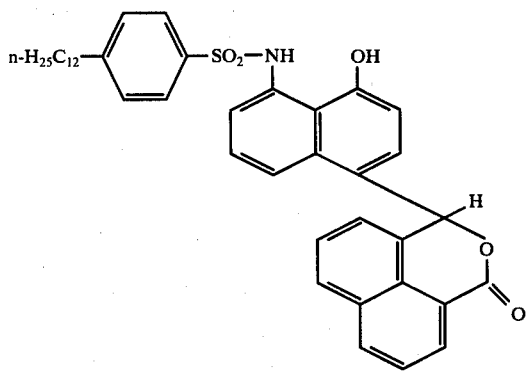

(90)

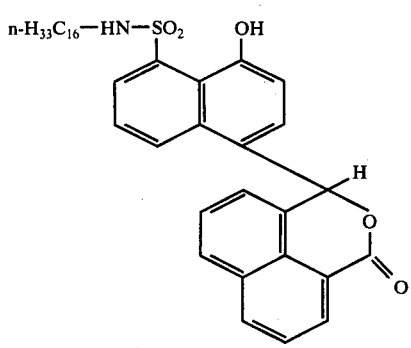

(91)

-continued

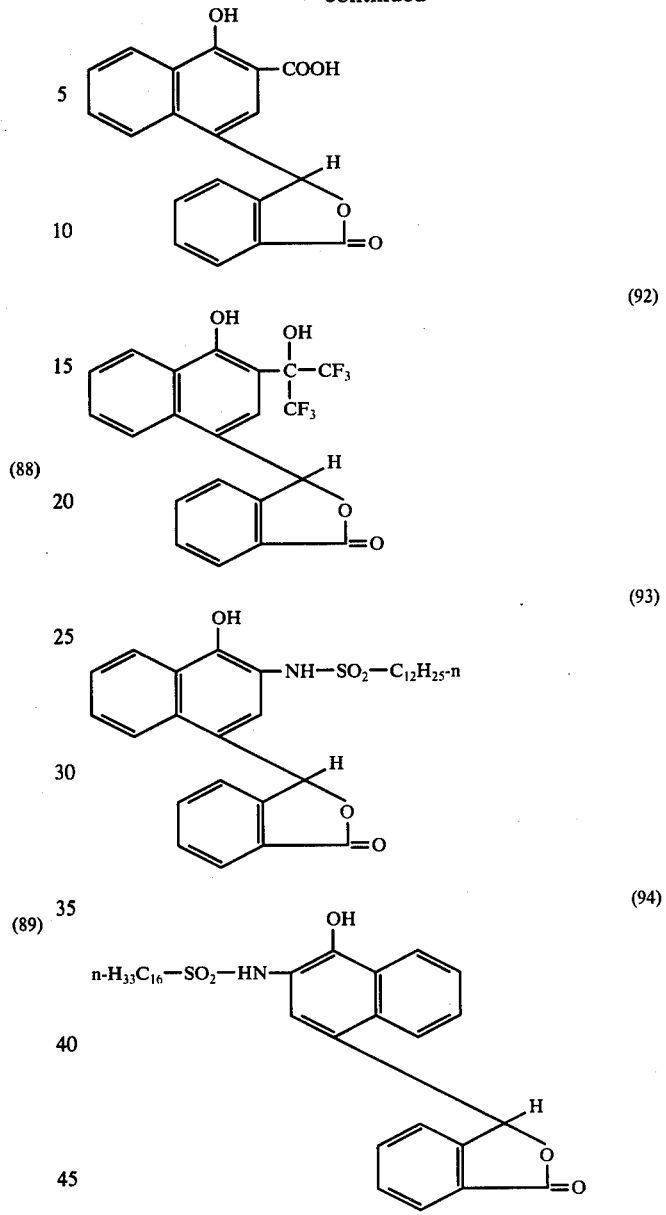

(92)

(93)

(94)

The p- (na)phthalidyl naphthol employed in step 1 of the present method may be prepared by reacting a 1-naphthol and the selected acid, i.e., the phthalaldehydic or naphthalaldehydic acid in substantially equimolar proportions in an organic solvent in the presence of a external acid catalyst, such as, zinc chloride, toluene-p-sulfonic acid, trifluoroacetic acid and trichloroacetic acid. Other suitable condensing acids include hydrochloric and sulfuric acids, preferably the anhydrous acids. For example, sulfuric acid has been used by Brubaker, et. al., J. Amer. Chem. Soc., 49, 2279 (1927) in the preparation of p-phthalidyl phenols by the condensation of certain phenolic compounds and o-phthalaldehydic acid. The aldehydic acid and the 1-naphthol may contain substituents provided, of course, that the 1-naphthol has a free position para to the naphtholic —OH for reaction with the (na)phthalaldehydic acid. The reaction temperature may vary over a relatively wide range from room temperature, i.e., about 20° C. up to elevated temperatures of about 120° C. which may be readily determined for the particular reactants. To achieve practical reaction rates, it is preferred to conduct the reaction at elevated temperatures but below temperatures at which decomposition of starting materials and/or side reactions and by-products tend to occur. The solvent used may be any of the inert organic liquids commonly employed for this condensation reaction, such as, glacial acetic acid, tetrahydrofuran, nitromethane, toluene, methylene chloride, and benzene.

In carrying out step 1 of the present method, the p-(na)phthalidyl naphthol and the 1-naphthol or indole are reacted in solution the presence of base at a pH of at least about the pKa, i.e. the dissociation constant of the (na)phthalidyl naphthol. In the case of naphthols, the pH selected is substantially the same as or above the pKa's of the (na)phthalidyl naphthol and 1-naphthol reactants. In the case of indoles which are good nucleophiles, the pH selected is approximately the same as the pKa of the (na)phthalidyl naphthol. Thus, the particular base and its concentration will be selected to provide the appropriate pH for the particular reactants employed. Ordinarily, the base in used in aqueous solution or in aqueous organic solution. For example, an aqueous or aqueous alkanol solution of between about 5% and 25% by weight sodium hydroxide has been found satisfactory for the reaction of a (na)phthalidyl naphthol and a 1-naphthol having pKa's in the vicinity of 12 to 14. It will be appreciated that other bases may be employed, for example, other hydroxides, such as, potassium and lithium hydroxides and that the base selected may be in organic and usually aqueous or aqueous-organic media as appropriate for forming a solution of the base and reactants.

The (na)phthalidyl naphthol may be reacted with equimolar amounts or with an excess of the 1-naphthol or indole, usually in the proportion of about 1.0 to 2.0 moles of naphthol or indole per mole of (na)phthalidyl naphthol. It will be understood that the 1-naphthol will have a free position para to the naphtholic —OH and that the indole will have a free 3-position for forming the corresponding 4'-hydroxy-1'-naphthyl and indol-3-yl B radical in the leuco intermediate and final dye product. The reaction temperature may vary over a relatively wide range, depending upon the reactants, and is usually between about 20° C. and 100° C. For example, the reaction of (na)phthalidyl naphthol and indole proceeds quite readily at room temperature whereas the reaction of the (na)phthalidyl compound with a 1-naphthol preferably is conducted at elevated temperatures of about 50° C. or higher. In the production of carboxy-naphthol dyes, a reaction temperature of between about 50° C. and 70° C. is preferred to achieve a practical reaction rate together with optimum product yields.

As noted previously, in the preparation of the dicarboxy-naphthol indicator dyes, the naphtholic —OH groups of the leuco dye intermediate obtained in step 1 preferably are ionized prior to oxidation of the intermediate to form the indicator. By ionizing the naphtholic groups first, the methane hydrogen may be removed more readily thereby facilitating the oxidation step. Ionization may be carried out in a known manner, for example, by treating with a basic reagent capable of ionizing the naphtholic groups in the solvent selected. Typical basic reagents include an organic base, such as, N, N, N', N'-tetramethyl-1,8-diaminonaphthalene or an inorganic base, such as, sodium hydroxide, sodium hydride, sodium methoxide, potassium hydroxide, and potassium t-butoxide. Sodium and potassium hydroxide, are generally used in aqueous solution. To achieve better yields, the ionization preferably is carried out in organic solution, for example, sodium methoxide in ethanol, potassium t-butoxide in t-butanol, and the tetramethyldiaminonaphthalene or sodium hydride or potassium t-butoxide in a non-protonic organic solvent, such as, dimethylsulfoxide, N,N-dimethyl-formamide or dimethoxyethane. It will be appreciated that it may be desirable to include the ionization step in the preparation of dyes other than the dicarboxy-naphthols to facilitate oxidation of the leuco dye intermediate, particularly where both the A and B radicals of the leuco dye are derived from naphthols.

The oxidation of step 2 may be carried out using any conventional oxidizing agent and is most conveniently carried out by simply adding the selected agent(s) to the reaction mixture containing the leuco dye or the ionized leuco dye intermediate. Examples of oxidizing agents that may be employed include gaseous oxygen, silver oxide, silver acetate, potassium persulfate, lead acetate, lead oxide, manganese dioxide, sodium chromate and potassium peroxydisulfate which oxidants are usually added to aqueous solutions of the intermediate. Oxidizing agents which ordinarily are added to organic solutions of intermediate include, for example, 2,3-dichloro-5,6-dicyano-1,4-benzoquinone, o-chloranil, and chloranil.

The ionization and oxidation steps may be carried out at room temperature or above and usually between about 20° C. and 100° C. The appropriate temperature for achieving optimum results may be readily determined for the particular leuco dye intermediate. Though not essential, any or all of the steps of the present method and preferably, the base-catalyzed addition of step 1 is conducted under an inert atmosphere, e.g., nitrogen.

In another embodiment, the general reaction scheme detailed above may be employed in the production of indicator dyes wherein the naphthalide ring-closing moiety is substituted with a sulfonamido substituent. In the production of such dyes, 6-nitronaphthalaldehydic acid is reacted with a 1-naphthol to form the corresponding 1:1 adduct. The nitro group is reduced to an amino group prior to step 1 and the amino group is converted to a sulfonamido group subsequent to step 2 as shown in the following sequence illustrating the preparation of a bis(3'-carboxy-4'-hydroxynaphthyl)-6-sulfonamidonaphthalides.

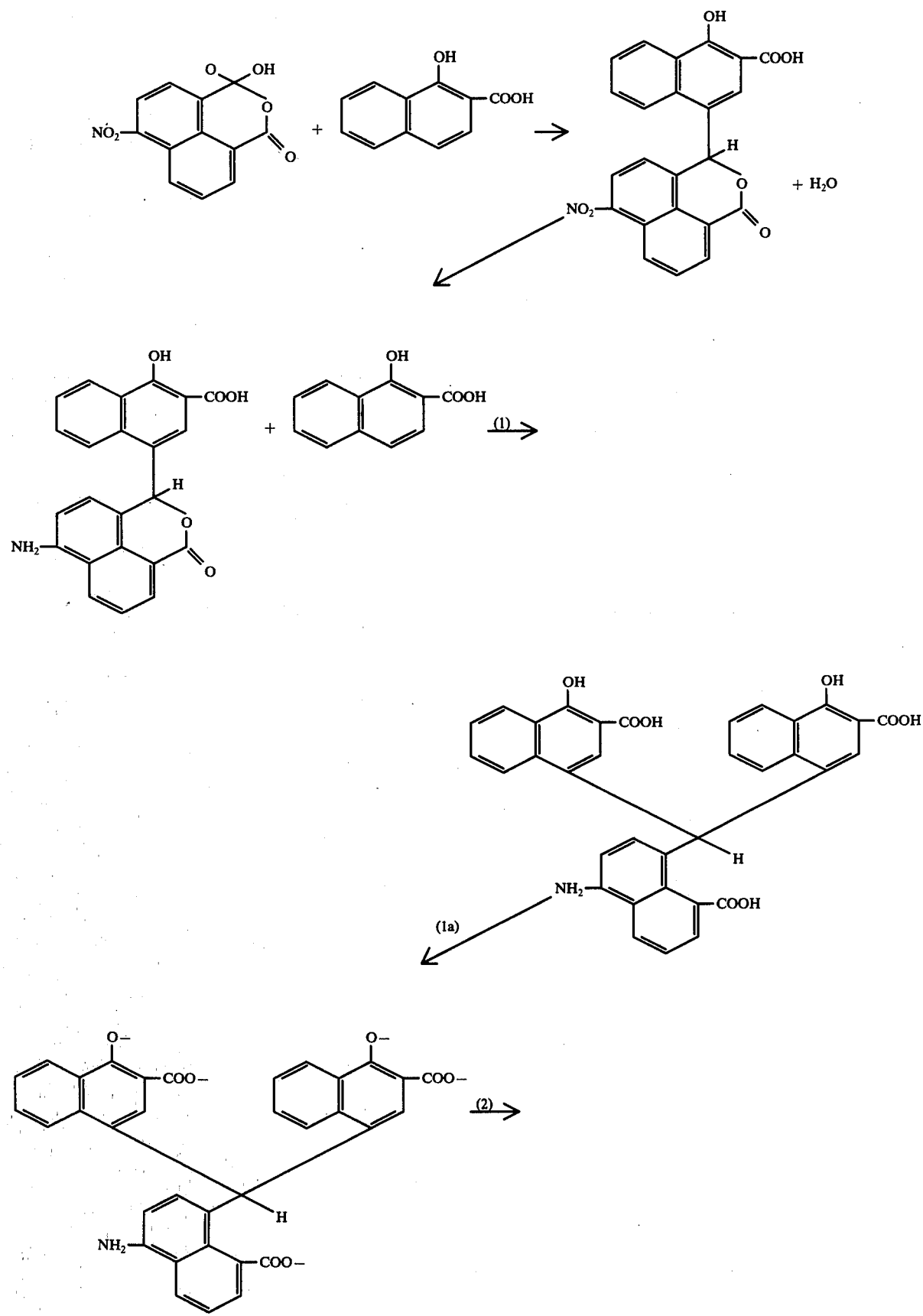

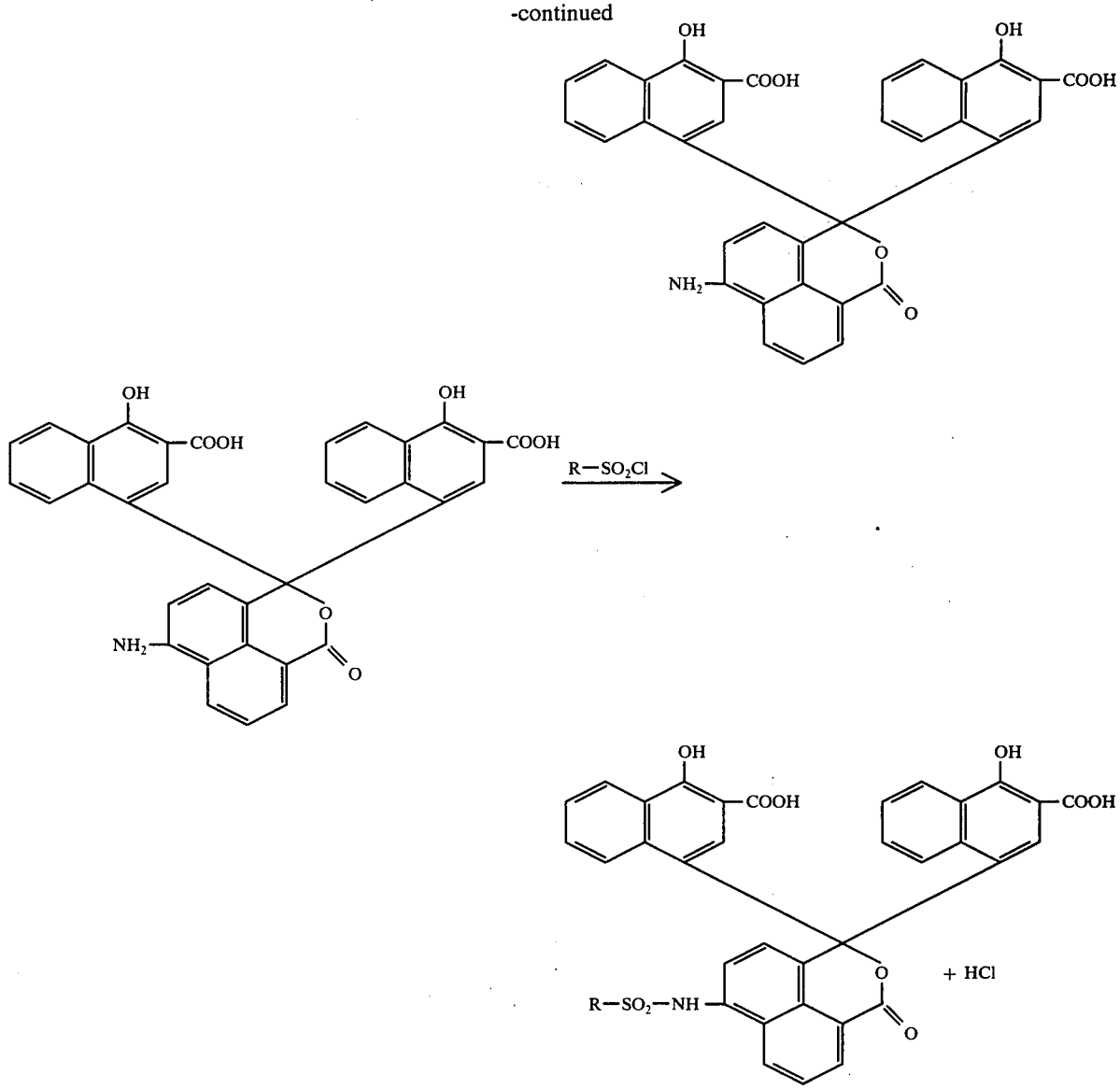

In the embodiment illustrated above, the 6-nitronaphthalaldehydic acid may be synthesized in a known manner by reacting naphthalaldehydic acid with potassium nitrate in sulfuric acid solution. After forming the 1:1 adduct with a 1-naphthol and prior to step 1, the nitro group may be reduced to an amino group by treating with a reducing agent such as stannous chloride, by introducing gaseous hydrogen in the presence of a hydrogenation catalyst or in any other suitable and convenient manner. Converting the amino group to a sulfonamido group also may be carried out in a conventional manner by reacting the selected sulfonyl chloride with the 6-aminonaphthalide indicator dye in aqueous and/or inert organic media and preferably, in aqueous media to facilitate isolation of the sulfonamido dye product.

The sulfonyl chloride (R—SO$_2$Cl) employed may contain as the R substituent, an alkyl, aryl, aralkyl or alkaryl group. Like R' and R'', the R group usually contains up to about 20 carbon atoms but may contain a greater number of carbon atoms as may be desired. For example, the sulfonamido group on the ring-closing portion of the dye provides a convenient means for adjusting the diffusibility of the dye in aqueous solution by selecting an R group to give the degree of mobility desired. The alkyl group or the alkyl portion of the alkaryl group may be branched or straight chain, and preferably is straight chain where the sulfonamido group is being utilized to render the dye substantially non-diffusible in the processing solution. Examples of groups that may comprise R include alkyl, such as, methyl, ethyl, propyl, isopropyl, sec-butyl, tert-butyl, hexyl, octyl, decyl, dodecyl, hexadecyl, octadecyl and eicosanyl; aryl, such as, phenyl and naphthyl; aralkyl and alkaryl, particularly phenyl-substituted alkyl and alkyl-substituted phenyl, such as, benzyl, phenethyl, phenylhexyl, p-hexylphenyl, p-octylphenyl and p-dodecylphenyl.

The following examples are given to further illustrate the present invention and are not intended to limit the scope thereof.

EXAMPLE 1

Preparation of the compound of Formula (29):

a. 13.1 g. of potassium nitrate was dissolved in 75 ml. of sulfuric acid. This solution was added dropwise to a cooled (5° C.) solution of 23.8 g. of naphthalaldehydic acid in 175 ml. of sulfuric acid, while maintaining the temperature at 50° C. throughout addition. The reaction mixture was refrigerated overnight. It was then poured into ice water (about 400 ml.). A light yellow solid was obtained. The solid was dissolved in about 500 ml. of 1,2-dimethoxyethane, and after evaporating the solvent down to about half the volume, 3-hydroxy-6-nitronaphthalide-1,8 was obtained as beige crystals.

b. A mixture of 3-hydroxy-6-nitronaphthalide-1,8 (6.12 g.; 0.025 m.) prepared above and 1-hydroxy-2-naphthoic acid (4.7 g.; 0.025 m.) in 100 ml. of 12% p-toluenesulfonic acid in acetic acid solution was heated to reflux. After about one hour the reactants were in solution and then a yellow solid formed. After refluxing for additional two hours, the reaction solution was cooled, and the yellow solid was removed by filtration and recrystallized from methyl cellosolve to yield 8.3 g. (67% by weight) of 3-(3'-carboxy-4'-hydroxynaphthyl)-6-nitronaphthalide-1,8, melting range 255° –258° C.

c. 3-(3'-carboxy-4'-hydroxy-1'-naphthyl)-6-nitronaphthalide-1,8 (4.15 g; 0.01 m.) as prepared in step (b) was heated in 120 ml. of methyl cellosolve until the naphthalide was dissolved. The resulting solution was cooled to room temperature. Stannous chloride (6.78 g,; 0.03 m.) dissolved in hydrochloric acid (20 ml.) was added dropwise to the solution, and the solution was stirred overnight at room temperature. The reaction mixture was poured into ethyl acetate (about 250 ml.) and the ethyl acetate solution extracted several times with water until some orange solid precipitated. Then the ethyl acetate was removed by evaporation leaving an orange oil that crystallized upon standing to yield 2.5 g. of the corresponding 6-aminonaphthalide. (65% by weight yield).

d. The 3-(3'-carboxy-4'-hydroxy-1'-naphthyl)-6-aminonaphthalide-1,8 prepared above (4.8 g.; 0.012 m.) and 1-hydroxy-2-naphthoic acid (4.5 g.; 0.024 m.) were added to a deareated aqueous sodium hydroxide solution (7.6% NaOH) under nitrogen. The resulting solution was heated to 70° C. for 5 hours after which time no aminonaphthalide remained. The solution was then poured into water and extracted several times at pH 8–10 with ethyl acetate to remove any remaining 1-hydroxy-2-naphthoic acid and at pH 6–8 to remove other impurities. The pH was then adjusted to below pH 6 by the addition of 10% aqueous hydrochloric acid. The solution was extracted with ethyl acetate and upon evaporation of the solvent, 4.95 g. of leuco compound was obtained (67.5% by weight yield).

e. To the leuco compound prepared above (9.5 g.; 0.017 m.) in 500 ml. of dimethylsulfoxide under nitrogen, was added portionwise a 50% solution of sodium hydride (4.1 g.; 0.017 m.) in oil. The mixture was heated to 60° C. for one hour until no more reaction was apparent. After cooling to room temperature, silver acetate (100 mg.) was added and then potassium persulfate (4.6 g.). Upon heating for 15 minutes, the mixture turned blue. The reaction mixture was then filtered over Celite, and ice water was added to the filtrate which was acidified with dilute hydrochloric acid. The flocculent beige solid that formed was extracted with ethyl acetate several times. The first two extracts yielded a small amount of grey solid impurity. Further extractions, upon evaporation of the ethyl acetate, gave a brown oil which when taken up in methanol and with water added, yielded the corresponding naphthalide compound as a yellow solid (6.5 g.; 68.4% by weight yielded).

f. 2.30 g. of 3,3-bis-(3'-carboxy-4'-hydroxy-1'-naphthyl)-6-amino-napthalide of step (e) was dissolved in water (25 ml.) and 1N aqueous sodium hydroxide solution (6 ml.). Acetone (10 ml.) was added and a combination pH electrode inserted. The pH was adjusted to 8.5 by adding 1N sodium hydroxide. The solution was stirred and para-n-dodecylbenzenesulfonyl chloride (1.40 g.) was added. The mixture was warmed to 40° C., and stirring was continued. The pH which had slowly dropped to about 7.5 was adjusted to 8.5 by adding 1N sodium hydroxide solution. The mixture was stirred overnight under nitrogen at 40° C. The pH which had dropped to about 3.5 was adjusted to 8.5 with 1N sodium hdyroxide and an additional 0.70 g. the sulfonyl chloride was added. Reaction was continued for about 8 hours with the pH reading held between 7.5 and 8.5. The mixture was then cooled and filtered to remove a crystalline solid. The filtrate was diluted with 100 ml. of water and mixed with 100 ml. of ethyl acetate. The pH of the mixture was adjusted to 7.0 with diltue hydrochoric acid. The layers were separated and the lower layer was stirred with 100 ml. of fresh ethyl acetate and the pH was adjusted to 6.0. The ethyl acetate layer was separated, washed with dilute hydrochloric acid and then washed with water The ethyl acetate solution was dried over magnesium sulfate; filtered and evaporated to give the title compound (0.60 g.).

EXAMPLE 2

Preparation of the compound of formula (22).

a. A mixture of 3.6 gms. of diisopropylethylamine and 3.6 gms. of n-propylamine was added dropwise to 7.3 gms. of 1-carbomethoxynaphthalene-2-sulfonyl chloride in 25 ml. of chloroform while maintaining the temperature between 50° and 60° C. The resulting solution was kept at 50°–60° C. for 15 minutes at which time a precipitate began to form. Heating was continued for an additional 30 minutes. The solution was then cooled, acidified with 10% hydrochloric acid and the chloroform evaporated. Three recrystallizations of the residue from benzene-hexane yielded about 4.5 gms. of 2-n-propylsulfamoyl-1-naphthol (melting range 61°–64° C.).

b. A mixture of 2.4 gms. of the sulfamoyl intermediate prepared in step (a) above and 1.8 gms. of naphthaldehydic acid were dissolved in 30 ml. of acetic acid and 30 ml. of 12% p-toluene sulfonic acid in acetic acid was added. The resulting solution was heated at reflux overnight. The reaction mixture was poured into an equal volume of cold water. The precipitate formed was collected and recrystallized from a benzene-petroleum ether mixture to yield 3.0 gms. of solid (melting range 189°–191° C.)

c. A solution of 50 ml. of aqueous 10% sodium hydroxide was flushed with nitrogen for 2 hours. To the solution was added 2.3 gms. of the product of step (b) and 1.4 gms. of 2-n-propyl-sulfamoyl-1-naphthol as prepared in step (a). The resulting solution was heated at 60° C. overnight. The temperature was raised to 70° C. and heating was continued for about 48 hours. The reaction mixture was then cooled and the pH adjusted to approximately 1.0 with dilute hydrochloric acid. The white solids formed were collected and washed and taken up in benzene. The benzene solution was treated with charcoal, filtered and concentrated until solids began to precipitate. The precipitate was collected yielding 2.5 gms. of white solid (melting range 178°–180° C. dec.).

d. 710 mgs. of the product of step (c) were dissolved in about 30 ml. of dimethylformamide. To this was added 230 mgs. of 57% sodium hydride. The resulting solution was heated at 80° C. until the evolution of hydrogen had ceased. Then 470 mgs. of silver oxide was added, and the mixture was stirred overnight at room temperature. Heating was continued at 80° C. for 8 hours. The reaction mixture was filtered, and the filtrate poured into 30 ml. of water, acidified with dilute hydrochloric acid and the precipitate collected. The precipitate was taken up in benzene and chromatographed on silica gel. Elution with 10% ethyl acetate in benzene yielded about 100 mgs. of the title compound.

EXAMPLE 3

Preparation of the compound of the formula (1).

a. A solution of 61 g. of sodium hydroxide and enough water to give 350 ml. of solution was purged by bubbling nitrogen through the solution. To this was added 30.0 g. of 3-(3'-carboxy-4'-hydroxy-1'-naphthyl)naphthalide and 10.0 g. of 1-hydroxy-2-naphthoic aicd (2-carboxy-1-naphthol). The solution was stirred and heated at 50° C. for 23 hours. An additional 5.0 of 1-hydroxy-2-naphthoic acid was added; the temperature increased to 70° C.; and heating continued 4 and ½ hours. The solution was cooled, mixed with 300 ml. of water and 400 ml. of ethylacetate. The pH of the stirred mixture was adjusted to 8.0 with aqueous hydrochloric acid. The ethylacetate was separated and discarded. This procedure was repeated. (The discared extracts contained mainly 1-hydroxy-2-naphthoic acid.) Another 400 ml. of ethyl acetate was added; the pH was adjusted to 6.5 with aqueous hydrocloric acid. The ethyl acetate was separated, washed with cold dilute hydrochloric acid, then with water, then dried over magnesium sulfate. Evaporation followed by ethyl acetate washing of the solid yielded 32.0 g. of leuco dye intermediate. This was satisfactory for conversion to the indicator dye but may be recrystallized from 50/50 ethyl acetate: 1,2-dimethoxyethane.

b. A solution of 9.97 g. of the above leuco dye intermediate in 170 ml. of molecular sieve dried dimethylsulfoxide was purged by bubbling nitrogen through it. The solution was treated with 4,37 g. of 54% by weight sodium hydride dispersion. When gas evolution had ceased, 4.84 g. of potassium peroxydisulfate was added all at once and the solution stirred for three and one-half hours. The solution was then made strongly acidic with aqueous hydrochloric acid, then diluted to 500 ml. with water. The tan solid which formed was collected and washed with water. The solid was dissolved in 300 ml. of water by adding aqueous sodium hydroxide solution to a pH of approximately 12. The solution was stirred with 300 ml. of ethyl acetate, and the ph was adjusted to 7.0 with dilute hydrochloric acid. The ethyl acetate was separated and discarded and the procedure was repeated beginning with the addition of 300 ml. of fresh ethyl acetate. The water later was then stirred, acidified to pH 1, and left overnight. The tan solid was collected and recrystallized from ethanol-water mixture to give 4.2 g. of the title compound as a white solid.

EXAMPLE 4

Preparation of the compound of the formula (35).

a. A solution containing 5.00 g. of 2-(o-hydroxyphenyl)indole, 9.20 g. of 3-(3'-carboxy-4'-hydroxy-1'-naphthyl) naphthalide and 3.95 g. of sodium hydroxide in 100 ml. of water was stirred overnight at room temperature under nitrogen. Some starting material remained. The solution was then heated for 2 hours at 50° C., cooled to 20° C., neutralized to pH 7, filtered and acidified to pH 1. The acidified solution was extracted with ethyl acetate. The ethyl acetate solution was washed with water, dried over magnesium sulfate and evaporated to an oil. Treatment of the oil with benzene produced the leuco dye intermediate as a white solid, yield 2.0 g.

b. To a solution of 1.0 g. of the above dye intermediate in 20 ml. of dry 1,2-dimethoxybenzene under nitrogen was added 0.40 g. of 2,3-dichloro-5,6-dicyanobenzoquinone. After heating one hour at reflux, the solution was cooled and the title compound separated as a nearly white solid, 0.40 g.

EXAMPLE 5

Preparation of the compound of the formula (36).

The title compound was prepared according to the procedure of Example 4 by reacting 5-n-dodecyloxy indole with 3-(3'-carboxy-4'-hydroxy-1'-naphthyl)naphthalide.

The 3-(3'-carboxy-4'-hydroxy-1'-naphthyl) naphthalide employed in Examples 3 to 5 was prepared as follows: Naphthalaldehydic acid, 40.0 g. (0.20 moles), 1-hydroxy-2-naphthoic acid, 37.6 g. (0.20 moles), and 12% p-toluenesulfonic acid in acetic acid (600 ml.) were mixed in a flask equipped with a stirrer and a reflux condenser closed by a calcium sulfate drying tube. The mixture was refluxed for 5 hours, poured into ice water and the resulting solid was collected by filtration, washed with water and air dried. The solid was recrystallized from methyl cellosolve to give 43 g. of the product, a nearly white crystalline solid.

It will be appreciated that other 1-naphthols such as those containing a hydrogen-bonding group substituted in the 2- or 8-position may be employed to provide the corresponding A or B radical in the above examples, and also, that other indoles, such as those substituted in the 2- or 7-position with a hydrogen bonding group may be employed to provide the corresponding B radical. For preparing phthalide, phthalaldehydic acid or phthalaldehydic acid substituted with, e.g., carboxy may be substituted for naphthalaldehydic acid in the above examples.

As noted previously, naphthol phthaleins and naphthaleins wherein on or both of the naphthol radicals is substituted with certain groups, such as, a carboxy group, form the subject matter of copending application Ser. No. 103,865 of Myron S. Simon filed January 4, 1971, now U.S. Pat. No. 3,833,614. Mixed phthaleins and naphthaleins comprising one indole radical and one p-hydroxycarbocyclic aryl radical derived from a phenol or a 1-naphthol comprise the subject matter of copending application Ser. No. 202,558 of Eva R. Karger and Paul T. MacGregor filed Nov. 26, 1971, now U.S. Pat. No. 3,816,124.

The indicator dyes produced in accordance with the present invention may be employed in analytical procedures where phthalein indicators are commonly used, for example, to measure changes in pH value and find other uses as well. As discussed in copending U.S. patent applications Ser. No. 108,260 filed Jan. 21, 1971, now U.S. Pat. No. 3,702,244 issued Nov. 7, 1972 and Ser. No. 103,392 filed Jan. 4, 1971, now U.S. Pat. No. 3,702,245 issued Nov. 7, 1972, it has been found that a selectively exposed photosensitive material having a latent image therein may be processed in the presence of extraneous incident radiation actinic thereto by reason of the protection afforded by suitably positioning with respect to the exposure surface of the photosensitive layer an effective concentration of a selected dye or dyes as optical filter agents. The use of certain indole dyes including indole phthalides and naphthalides as optical filter agents for protecting photosensitive materials from radiation in the shorter wavelength region of the visible spectrum forms the subject matter of aforementioned application Ser. No. 108,260. The use of certain dyes derived from phenolic compounds including 1-naphthol phthalides and naphthalides as optical filter agents for protecting photosensitive materials from radiation in the longer wavelength region of the visible spectrum forms the subject matter of aforementioned application Ser. No. 103,392.

Since certain changes may be made in the above process and products without departing from the scope of the invention herein involved, it is intended that all matter contained in the above description shall be interpreted as illustrative and not in a limiting sense.

What is claimed is:

1. A compound of the formula:

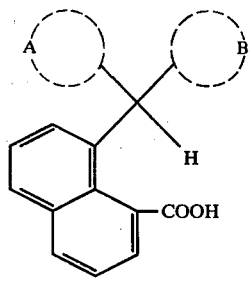

wherein A represent 4'-hydroxy-1'-naphthyl and B represents 4'-hydroxy-1'-naphthyl.

2. A compound as defined in claim 1 wherein said B represents 4'-hydroxy-1'-naphthyl.

3. A compound as defined in claim 2 wherein said 4'-hydroxy-1'-naphthyl A is substituted in the 3'- or 5'-position with a hydrogen-bonding group.

4. A compound as defined in claim 3 wherein said hydrogen-bonding group is substituted in the 3'position.

5. A compound as defined in claim 2 wherein said 4'-hydroxy-1'-naphthyl B is substituted in the 3'- or 5'-position with a hydrogen-bonding group.

6. A compound of the formula:

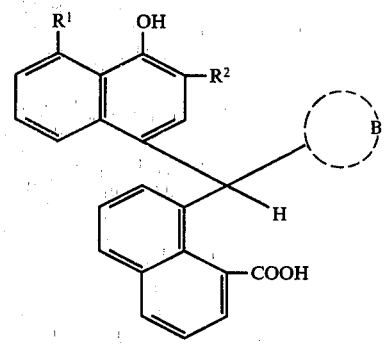

wherein $R^1$ and $R^2$ each are selected from hydrogen and a hydrogen-bonding group selected from carboxy, hydroxy, o-hydroxyphenyl, bis trifluoromethyl carbinol, sulfonamido and sulfamoyl, at least one of $R^1$ and $R^2$ being hydrogen, and B is

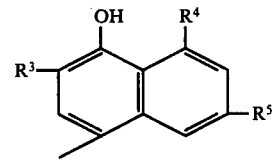

wherein $R^3$ and $R^4$ have the same meaning given for $R^1$ and $R^2$, and $R^5$ is hydrogen or alkoxy containing 1 to 18 carbon atoms.

7. A compound as defined in claim 6 wherein $R^1$ is hydrogen and $R^2$ is a hydrogen-bonding group.

8. A compound as defined in claim 7 wherein said B is

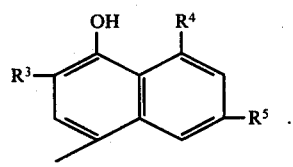

9. A compound as defined in claim 8 wherein $R^4$ is hydrogen and $R^3$ is a hydrogen-bonding group.

10. A compound as defined in claim 9 wherein $R^2$ is carboxy and $R^3$ is carboxy.

11. A compound as defined in claim 9 wherein $R^2$ is sulfamoyl and $R^3$ is sulfamoyl.

12. The compound of the formula:

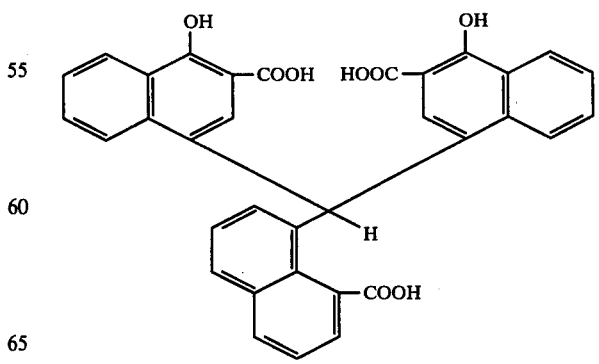

13. The compound of the formula:

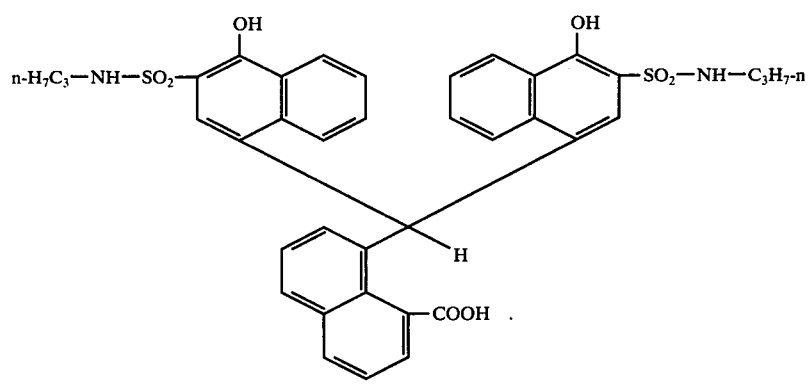
* * * * *